(12) United States Patent
Boone et al.

(10) Patent No.: US 8,168,416 B2
(45) Date of Patent: May 1, 2012

(54) MODIFIED LECITHIN-CHOLESTEROL ACYLTRANSFERASE ENZYMES

(75) Inventors: Tom Boone, Newbury Park, CA (US); David Park Meininger, Seattle, WA (US); Margrit Schwarz, San Carlos, CA (US); Bei Shan, Redwood City, CA (US); Wenyan Shen, Wayne, PA (US); Mingyue Zhou, Hayward, CA (US)

(73) Assignee: Amgen Inc., Thousand Oaks, CA (US)

( * ) Notice: Subject to any disclaimer, the term of this patent is extended or adjusted under 35 U.S.C. 154(b) by 12 days.

(21) Appl. No.: 12/179,815

(22) Filed: Jul. 25, 2008

(65) Prior Publication Data

US 2009/0081182 A1   Mar. 26, 2009

Related U.S. Application Data

(60) Provisional application No. 60/952,007, filed on Jul. 26, 2007.

(51) Int. Cl.
*C12N 9/10* (2006.01)
*A61K 38/45* (2006.01)
*A61P 9/00* (2006.01)
*C12P 21/02* (2006.01)

(52) U.S. Cl. .......... 435/193; 514/1.9; 514/7.4; 435/69.1

(58) Field of Classification Search .................. 435/193, 435/69.1; 514/1.9, 7.4
See application file for complete search history.

(56) References Cited

U.S. PATENT DOCUMENTS 6,498,019 B1 * 12/2002 Taniyama ................. 435/69.1

FOREIGN PATENT DOCUMENTS

| WO | WO-97/17434 | 5/1997 |
|----|-------------|--------|
| WO | WO-01/05943 A2 | 1/2001 |
| WO | WO-2008/002591 | 1/2008 |

OTHER PUBLICATIONS

Hengstschläger-Ottnad et al., "Chicken lecithin-cholesterol acyltransferase molecular characterization reveals unusual structure and expression patterns," J Biol Chem 270(44):26139-26145, 1995.*
Result 5, PIR protein database search, alignment of instant SEQ ID No. 1 with the chicken LCAT sequence of Hengstschläger-Ottnad et al. (J Biol Chem 270(44):26139-26145, 1995), performed on Mar. 23, 2010.*
French et al., "What is a conservative substitution?" J Mol Evol 19:171-175, 1983.*
Results 5-9, alignment of instant SEQ ID No. 1 with SEQ ID Nos. 1, 4, 6 of Taniyama (US 6498019), search in protein database of issued US patents, Mar. 23, 2010.*
Francone, et al. "Effects of site-directed mutagenesis at residues cysteine-31 and cysteine-184 on lecithin-cholesterol acyltransferase activity," Proc. Natl. Acad. Sci. USA, 88:1716-1720 (1991).
Hengstschlager-Ottnad, et al. "Chicken Lecithin-Cholesterol Acyltransferase," The Journal of Biological Chemistry, 270(44):26139-26145 (1995).
International Search Report om PCT/US2008/071119 dated Jan. 26, 2009.
Wang, et al. "Importance of the free sulfhydryl groups of lecithin-cholesterol acyltransferase for its sensitivity to oxidative inactivation," Biochimica et Biophysica Acta 1488:268-277 (2000).
Qu et al., Roles of cysteines in human lecithin: Cholesterol acyltransferase. *Biochemistry*, 32: 3089-94 (2003).
Search Report and Written Opinion of the Australian Patent Office issued in connection with Singapore Patent Application No. 201000383-8, dated Mar. 22, 2011.
Genbank Accession No. AAB34898, Lecithin: Choleterol acyltransferase, LCAT [human, plasma, Peptide, 416 aa], dated Sep. 27, 1995.
Genbank Accession No. AAA59499, Lecithin: Cholesterol acyltransferase precursor [*Homo sapiens*], dated Jan. 7, 1995.

* cited by examiner

*Primary Examiner* — Rosanne Kosson
(74) *Attorney, Agent, or Firm* — Marshall, Gerstein & Borun LLP; Olga Mekhovich; Scott Ausenhus

(57) ABSTRACT

The invention provides compounds, pharmaceutical compositions and methods for treating atherosclerosis, coronary heart disease, thrombosis, and for decreasing or prevention of accumulation of cholesterol in a subject by modifying LCAT polypeptide.

69 Claims, 10 Drawing Sheets

FIGURE 1A

AAB20750 lecithin:cholesterol acyltransferase; LCAT [Homo sapiens]

AAB34898 lecithin:cholesterol acyltransferase, LCAT [human, plasma, Peptide, 416 aa]

AAA59499 lecithin:cholesterol acyltransferase precursor

AAA59500 lecithin-cholesterol acyltransferase precursor (EC 2.3.1.43)

AAL11035 lecithin-cholesterol acyltransferase Lcat [Mus musculus]

P04180 Phosphatidylcholine-sterol acyltransferase precursor (Lecithin-cholesterol acyltransferase) (Phospholipid-cholesterol acyltransferase)

NP_000220 lecithin-cholesterol acyltransferase precursor [Homo sapiens]

NP_032516 lecithin cholesterol acyltransferase [Mus musculus]

NP_058720 lecithin cholesterol acyltransferase [Rattus norvegicus]

P53761 Phosphatidylcholine-sterol acyltransferase precursor (Lecithin-cholesterol acyltransferase) (Phospholipid-cholesterol acyltransferase)

NP_001075659 lecithin-cholesterol acyltransferase [Oryctolagus cuniculus]

O35840 Phosphatidylcholine-sterol acyltransferase (Lecithin-cholesterol acyltransferase) (Phospholipid-cholesterol acyltransferase)

O35573 Phosphatidylcholine-sterol acyltransferase (Lecithin-cholesterol acyltransferase) (Phospholipid-cholesterol acyltransferase)

Q08758 Phosphatidylcholine-sterol acyltransferase precursor (Lecithin-cholesterol acyltransferase) (Phospholipid-cholesterol acyltransferase)

P18424 Phosphatidylcholine-sterol acyltransferase precursor (Lecithin-cholesterol acyltransferase) (Phospholipid-cholesterol acyltransferase)

P30930_11 [Segment 11 of 11] Phosphatidylcholine-sterol acyltransferase (Lecithin-cholesterol acyltransferase) (Phospholipid-cholesterol acyltransferase)

P30930_10 [Segment 10 of 11] Phosphatidylcholine-sterol acyltransferase (Lecithin-cholesterol acyltransferase) (Phospholipid-cholesterol acyltransferase)

P30930_9 [Segment 9 of 11] Phosphatidylcholine-sterol acyltransferase (Lecithin-cholesterol acyltransferase) (Phospholipid-cholesterol acyltransferase)

FIGURE 1B

P30930_8 [Segment 8 of 11] Phosphatidylcholine-sterol acyltransferase (Lecithin-cholesterol acyltransferase) (Phospholipid-cholesterol acyltransferase)

P30930_7 [Segment 7 of 11] Phosphatidylcholine-sterol acyltransferase (Lecithin-cholesterol acyltransferase) (Phospholipid-cholesterol acyltransferase)

P30930_6 [Segment 6 of 11] Phosphatidylcholine-sterol acyltransferase (Lecithin-cholesterol acyltransferase) (Phospholipid-cholesterol acyltransferase)

P30930_5 [Segment 5 of 11] Phosphatidylcholine-sterol acyltransferase (Lecithin-cholesterol acyltransferase) (Phospholipid-cholesterol acyltransferase)

P30930_4 [Segment 4 of 11] Phosphatidylcholine-sterol acyltransferase (Lecithin-cholesterol acyltransferase) (Phospholipid-cholesterol acyltransferase)

P30930_3 [Segment 3 of 11] Phosphatidylcholine-sterol acyltransferase (Lecithin-cholesterol acyltransferase) (Phospholipid-cholesterol acyltransferase)

P30930_2 [Segment 2 of 11] Phosphatidylcholine-sterol acyltransferase (Lecithin-cholesterol acyltransferase) (Phospholipid-cholesterol acyltransferase)

P30930_1 [Segment 1 of 11] Phosphatidylcholine-sterol acyltransferase (Lecithin-cholesterol acyltransferase) (Phospholipid-cholesterol acyltransferase)

P30930 Phosphatidylcholine-sterol acyltransferase (Lecithin-cholesterol acyltransferase) (Phospholipid-cholesterol acyltransferase)

O35724 Phosphatidylcholine-sterol acyltransferase (Lecithin-cholesterol acyltransferase) (Phospholipid-cholesterol acyltransferase)

O35502 Phosphatidylcholine-sterol acyltransferase (Lecithin-cholesterol acyltransferase) (Phospholipid-cholesterol acyltransferase)

AAG22588 lecithin:cholesterol acyl-transferase [Cavia porcellus]

AAG22587 lecithin:cholesterol acyl-transferase [Crocidura russula]

AAG22586 lecithin:cholesterol acyl-transferase [Didelphis marsupialis]

AAB58992 lecithin:cholesterol acyl transferase [Microtus nivalis]

AAG21089 lecithin: cholesterol acyl-transferase [Erinaceus europaeus]

AAG21088 lecithin: cholesterol acyl-transferase [Didelphis marsupialis]

AAG21087 lecithin: cholesterol acyl-transferase [Cavia porcellus]

CAB56610 lectin cholesterol acyltransferase [Homo sapiens]

AAD28484 lecithin-cholesterol acyltransferase [Homo sapiens]

FIGURE 1C

AAB88662 lecithin:cholesterol acyl transferase [Akodon torques]

AAB60791 lecithin:cholesterol acyl transferase [Marmota marmota]

AAB59002 lecithin:cholesterol acyl transferase [Octodon lunatus]

AAB59001 lecithin:cholesterol acyl transferase [Sciurus griseus]

AAB59000 lecithin:cholesterol acyl transferase [Myoxus glis]

AAB58999 lecithin:cholesterol acyl transferase [Eliomys quercinus]

AAB58998 lecithin-cholesterol acyl transferase [Rhizomys pruinosus]

AAB58997 lecithin:cholesterol acyl transferase [Nannospalax leucodon]

AAB58996 lecithin:cholesterol acyl transferase [Spalax ehrenbergi]

AAB58994 lecithin:cholesterol acyl transferase [Peromyscus maniculatus]

AAB58993 lecithin:cholesterol acyl transferase [Cricetulus migratorius]

AAB58990 lecithin:cholesterol acyl transferase [Clethrionomys glareolus]

AAB58989 lecithin-cholesterol acyl transferase [Tatera kempi gambiana]

AAB58988 lecithin-cholesterol acyl transferase [Micromys minutus]

EDL92427 lecithin cholesterol acyltransferase, isoform CRA_e [Rattus norvegicus]

EDL92426 lecithin cholesterol acyltransferase, isoform CRA_d [Rattus norvegicus]

EDL92425 lecithin cholesterol acyltransferase, isoform CRA_c [Rattus norvegicus]

EDL92424 lecithin cholesterol acyltransferase, isoform CRA_b [Rattus norvegicus]

EDL92423 lecithin cholesterol acyltransferase, isoform CRA_a [Rattus norvegicus]

P53760 Phosphatidylcholine-sterol acyltransferase precursor (Lecithin-cholesterol acyltransferase) (Phospholipid-cholesterol acyltransferase)

P16301 Phosphatidylcholine-sterol acyltransferase precursor (Lecithin-cholesterol acyltransferase) (Phospholipid-cholesterol acyltransferase)

ABN42857 lecithin cholesterol acyltransferase [Peromyscus leucopus]

ABN42856 lecithin cholesterol acyltransferase [Peromyscus maniculatus]

ABN42855 lecithin cholesterol acyltransferase [Peromyscus maniculatus]

ABN42854 lecithin cholesterol acyltransferase [Peromyscus maniculatus]

FIGURE 1D

ABN42853 lecithin cholesterol acyltransferase [Peromyscus maniculatus]

ABN42852 lecithin cholesterol acyltransferase [Peromyscus maniculatus]

ABN42851 lecithin cholesterol acyltransferase [Peromyscus maniculatus]

ABN42850 lecithin cholesterol acyltransferase [Peromyscus maniculatus]

ABN42849 lecithin cholesterol acyltransferase [Peromyscus maniculatus]

ABN42848 lecithin cholesterol acyltransferase [Peromyscus maniculatus]

ABN42847 lecithin cholesterol acyltransferase [Peromyscus maniculatus]

ABN42846 lecithin cholesterol acyltransferase [Peromyscus maniculatus]

ABN42845 lecithin cholesterol acyltransferase [Peromyscus maniculatus]

ABN42844 lecithin cholesterol acyltransferase [Peromyscus maniculatus]

ABN42843 lecithin cholesterol acyltransferase [Peromyscus maniculatus]

ABN42842 lecithin cholesterol acyltransferase [Peromyscus maniculatus]

ABN42841 lecithin cholesterol acyltransferase [Peromyscus maniculatus]

ABN42840 lecithin cholesterol acyltransferase [Peromyscus maniculatus]

ABN42839 lecithin cholesterol acyltransferase [Peromyscus maniculatus]

ABN42838 lecithin cholesterol acyltransferase [Peromyscus maniculatus]

ABN42837 lecithin cholesterol acyltransferase [Peromyscus maniculatus]

ABN42836 lecithin cholesterol acyltransferase [Peromyscus maniculatus]

ABN42835 lecithin cholesterol acyltransferase [Peromyscus maniculatus]

ABN42834 lecithin cholesterol acyltransferase [Peromyscus maniculatus]

ABN42833 lecithin cholesterol acyltransferase [Peromyscus maniculatus]

ABN42832 lecithin cholesterol acyltransferase [Peromyscus maniculatus]

ABN42831 lecithin cholesterol acyltransferase [Peromyscus maniculatus]

ABN42830 lecithin cholesterol acyltransferase [Peromyscus maniculatus]

ABN42829 lecithin cholesterol acyltransferase [Peromyscus maniculatus]

FIGURE 1E

ABN42828 lecithin cholesterol acyltransferase [Peromyscus maniculatus]

ABN42827 lecithin cholesterol acyltransferase [Peromyscus maniculatus]

ABN42826 lecithin cholesterol acyltransferase [Peromyscus maniculatus]

ABN42825 lecithin cholesterol acyltransferase [Peromyscus maniculatus]

ABN42824 lecithin cholesterol acyltransferase [Peromyscus maniculatus]

ABN42823 lecithin cholesterol acyltransferase [Peromyscus maniculatus]

ABN42822 lecithin cholesterol acyltransferase [Peromyscus maniculatus]

ABN42821 lecithin cholesterol acyltransferase [Peromyscus maniculatus]

ABN42820 lecithin cholesterol acyltransferase [Peromyscus maniculatus]

ABN42819 lecithin cholesterol acyltransferase [Peromyscus maniculatus]

ABN42818 lecithin cholesterol acyltransferase [Peromyscus maniculatus]

ABN42817 lecithin cholesterol acyltransferase [Peromyscus maniculatus]

ABN42816 lecithin cholesterol acyltransferase [Peromyscus maniculatus]

ABN42815 lecithin cholesterol acyltransferase [Peromyscus maniculatus]

ABN42814 lecithin cholesterol acyltransferase [Peromyscus maniculatus]

ABN42813 lecithin cholesterol acyltransferase [Peromyscus maniculatus]

ABN42812 lecithin cholesterol acyltransferase [Peromyscus maniculatus]

ABN42811 lecithin cholesterol acyltransferase [Peromyscus maniculatus]

ABN42810 lecithin cholesterol acyltransferase [Peromyscus maniculatus]

ABN42809 lecithin cholesterol acyltransferase [Peromyscus maniculatus]

ABN42808 lecithin cholesterol acyltransferase [Peromyscus maniculatus]

ABN42807 lecithin cholesterol acyltransferase [Peromyscus maniculatus]

ABN42806 lecithin cholesterol acyltransferase [Peromyscus maniculatus]

ABN42805 lecithin cholesterol acyltransferase [Peromyscus maniculatus]

ABN42804 lecithin cholesterol acyltransferase [Peromyscus maniculatus]

ABN42803 lecithin cholesterol acyltransferase [Peromyscus maniculatus]

FIGURE 1F

EDL11335 lecithin cholesterol acyltransferase, isoform CRA_b [Mus musculus]

EDL11334 lecithin cholesterol acyltransferase, isoform CRA_a [Mus musculus]

EAW83190 lecithin-cholesterol acyltransferase [Homo sapiens]

NP_001005715 lecithin-cholesterol acyltransferase [Xenopus tropicalis]

CAD67533 lecithin cholesterol acyl transferase [Myomimus roachi]

CAD67541 lecithin cholesterol acyl transferase [Graphiurus lorraineus]

CAD67540 lecithin cholesterol acyl transferase [Graphiurus parvus]

CAD67539 lecithin cholesterol acyl transferase [Graphiurus ocularis]

CAD67534 lecithin cholesterol acyl transferase [Graphiurus platyops]

CAD67538 lecithin cholesterol acyl transferase [Graphiurus microtis]

CAD67537 lecithin cholesterol acyl transferase [Graphiurus murinus]

CAD67532 lecithin cholesterol acyl transferase [Dryomys laniger]

CAD67536 lecithin cholesterol acyl transferase [Eliomys melanurus]

CAD67535 lecithin cholesterol acyl transferase [Aplodontia rufa]

ABH06074 lecithin cholesterol acyltransferase [Onychomys torridus]

ABH06073 lecithin cholesterol acyltransferase [Onychomys torridus]

ABH06072 lecithin cholesterol acyltransferase [Peromyscus californicus]

ABH06071 lecithin cholesterol acyltransferase [Peromyscus californicus]

ABH06070 lecithin cholesterol acyltransferase [Peromyscus californicus]

ABH06069 lecithin cholesterol acyltransferase [Peromyscus californicus]

ABH06068 lecithin cholesterol acyltransferase [Peromyscus fraterculus]

ABH06067 lecithin cholesterol acyltransferase [Peromyscus eva]

ABH06066 lecithin cholesterol acyltransferase [Peromyscus eva]

ABH06065 lecithin cholesterol acyltransferase [Peromyscus melanophrys]

ABH06064 lecithin cholesterol acyltransferase [Peromyscus melanophrys]

FIGURE 1G

ABH06063 lecithin cholesterol acyltransferase [Peromyscus melanophrys]

ABH06062 lecithin cholesterol acyltransferase [Peromyscus aztecus]

ABH06061 lecithin cholesterol acyltransferase [Peromyscus aztecus]

ABH06060 lecithin cholesterol acyltransferase [Peromyscus aztecus]

ABH06059 lecithin cholesterol acyltransferase [Peromyscus mexicanus]

ABH06058 lecithin cholesterol acyltransferase [Peromyscus mexicanus]

ABH06057 lecithin cholesterol acyltransferase [Peromyscus mexicanus]

ABH06056 lecithin cholesterol acyltransferase [Peromyscus mexicanus]

ABH06055 lecithin cholesterol acyltransferase [Peromyscus truei]

ABH06054 lecithin cholesterol acyltransferase [Peromyscus truei]

ABH06053 lecithin cholesterol acyltransferase [Peromyscus truei]

ABH06052 lecithin cholesterol acyltransferase [Peromyscus boylii]

ABH06051 lecithin cholesterol acyltransferase [Peromyscus boylii]

ABH06050 lecithin cholesterol acyltransferase [Peromyscus boylii]

ABH06049 lecithin cholesterol acyltransferase [Peromyscus boylii]

ABH06048 lecithin cholesterol acyltransferase [Peromyscus gossypinus]

ABH06047 lecithin cholesterol acyltransferase [Peromyscus gossypinus]

ABH06046 lecithin cholesterol acyltransferase [Peromyscus gossypinus]

ABH06045 lecithin cholesterol acyltransferase [Peromyscus leucopus]

ABH06044 lecithin cholesterol acyltransferase [Peromyscus leucopus]

ABH06043 lecithin cholesterol acyltransferase [Peromyscus leucopus]

ABH06042 lecithin cholesterol acyltransferase [Peromyscus maniculatus]

ABH06041 lecithin cholesterol acyltransferase [Peromyscus maniculatus]

ABH06040 lecithin cholesterol acyltransferase [Peromyscus maniculatus]

ABH06039 lecithin cholesterol acyltransferase [Peromyscus maniculatus]

ABH06038 lecithin cholesterol acyltransferase [Peromyscus maniculatus]

FIGURE 1H

ABH06037 lecithin cholesterol acyltransferase [Peromyscus maniculatus]

ABH06036 lecithin cholesterol acyltransferase [Peromyscus difficilis]

ABH06035 lecithin cholesterol acyltransferase [Peromyscus difficilis]

ABH06034 lecithin cholesterol acyltransferase [Peromyscus difficilis]

ABH06033 lecithin cholesterol acyltransferase [Peromyscus difficilis]

ABH06032 lecithin cholesterol acyltransferase [Peromyscus eremicus]

ABH06031 lecithin cholesterol acyltransferase [Peromyscus eremicus]

ABH06030 lecithin cholesterol acyltransferase [Peromyscus eremicus]

ABH06029 lecithin cholesterol acyltransferase [Peromyscus crinitus]

ABH06028 lecithin cholesterol acyltransferase [Peromyscus crinitus]

ABH06027 lecithin cholesterol acyltransferase [Peromyscus crinitus]

ABH06026 lecithin cholesterol acyltransferase [Peromyscus crinitus]

ABH06025 lecithin cholesterol acyltransferase [Peromyscus polionotus]

ABH06024 lecithin cholesterol acyltransferase [Peromyscus polionotus]

ABH06023 lecithin cholesterol acyltransferase [Peromyscus polionotus]

ABH06022 lecithin cholesterol acyltransferase [Peromyscus polionotus]

ABH06021 lecithin cholesterol acyltransferase [Peromyscus polionotus]

ABH06020 lecithin cholesterol acyltransferase [Peromyscus polionotus]

AAH91155 Lecithin cholesterol acyltransferase [Rattus norvegicus]

AAH75304 Lecithin-cholesterol acyltransferase [Xenopus tropicalis]

AAH28861 Lecithin cholesterol acyltransferase [Mus musculus]

AAH14781 Lecithin-cholesterol acyltransferase [Homo sapiens]

AAR03499 lecithin-cholesterol acyltransferase [Homo sapiens]

AAF00979 lecithin cholesterol acyltransferase [Mus musculus]

AAD40188 lecithin-cholesterol acyltransferase [Rattus norvegicus]

FIGURE 1I

AAB86630 lecithin:cholesterol acyltransferase [Canis familiaris]

AAA59498 lecithin-cholesterol acyltransferase precursor (EC 2.3.1.43)

CAA28651 lecithin-cholesterol acyltransferase (LCAT) [Homo sapiens]

CAA38029 Lecithin cholesterol acyl transferase (LCAT); phosphatidylcholine--sterol acyltransferase [Mus musculus]

BAA02839 lecithin-cholesterol acyltransferase precursor [Oryctolagus cuniculus]

AAB65771 lecithin:cholesterol acyltransferase [Rattus norvegicus]

CAC18111 lecithin cholesterol acyl transferase [Acomys cahirinus]

CAC18236 lecithin cholesterol acyl transferase [Uranomys ruddi]

CAC18121 lecithin cholesterol acyl transferase [Mesocricetus auratus]

CAC18122 lecithin cholesterol acyl transferase [Macrotarsomys ingens]

CAC18114 lecithin cholesterol acyl transferase [Deomys ferrugineus]

CAC18130 lecithin cholesterol acyl transferase [Steatomys sp.]

CAC18118 lecithin cholesterol acyl transferase [Jaculus jaculus]

CAC18129 lecithin cholesterol acyl transferase [Sicista kazbegica]

CAC18124 lecithin cholesterol acyl transferase [Neotoma fuscipes]

CAC18127 lecithin cholesterol acyl transferase [Otomys angoniensis]

CAC18119 lecithin cholesterol acyl transferase [Lophuromys sikapusi]

CAC18123 lecithin cholesterol acyl transferase [Myospalax sp.]

CAC18128 lecithin cholesterol acyl transferase [Phodopus roborovskii]

CAC18126 lecithin cholesterol acyl transferase [Nesomys rufus]

CAC18120 lecithin cholesterol acyl transferase [Mystromys albicaudatus]

CAC18125 lecithin cholesterol acyl transferase [Napaeozapus insignis]

CAC18117 lecithin cholesterol acyl transferase [Dicrostonyx torquatus]

CAC18115 lecithin cholesterol acyl transferase [Dendromus mystacalis]

CAC18116 lecithin cholesterol acyl transferase [Dipus sagitta]

FIGURE 1J

CAC18113 lecithin cholesterol acyl transferase [Calomyscus mystax]

CAC18112 Lecithin-cholesterol acyl transferase [Allactaga elater]

AAQ10316 lecithine cholesterol acyltransferase-like protein [Medicago truncatula]

AAQ24609 lecithin-cholesterol acyltransferase [Sus scrofa domestica]

AAB58991 lecithin:cholesterol acyl transferase [Microtus nivalis]

AAB60792 lecithin:cholesterol acyl transferase [Myocastor coypus]

AAB60790 lecithin:cholesterol acyl transferase [Gerbillus henleyi]

AAB59003 lecithin:cholesterol acyl transferase [Octodon lunatus]

AAB58995 lecithin:cholesterol acyl transferase [Peromyscus maniculatus]

AAA35388 lecithin cholesterol acyltransferase

MODIFIED LECITHIN-CHOLESTEROL ACYLTRANSFERASE ENZYMES

FIELD OF THE INVENTION

This invention relates generally to the field of medicine and, more specifically, to compositions and methods for treating coronary heart disease, atherosclerosis, inflammatory disorders and disorders associated with thrombosis.

BACKGROUND OF THE INVENTION

Over 50 million Americans have cardiovascular problems, and many other countries face high and increasing rates of cardiovascular disease. It is the number one cause of death and disability in the United States and most European countries. By the time that heart problems are detected, the underlying cause, atherosclerosis, is usually quite advanced, having progressed for decades.

Atherosclerosis is a polygenic complex disease of mammals characterized by the deposits or plaques of lipids and other blood derivatives in the arterial walls (aorta, coronary arteries, and carotid). These plaques can be calcified to a greater or lesser extent according to the progression of the process. They are also associated with the accumulation of fatty deposits consisting mainly of cholesterol esters in the arteries. Cholesterol accumulates in the foam cells of the arterial wall, thereby narrowing the lumen and decreasing the flow of blood. This is accompanied by a thickening of the arterial wall, with hypertrophy of the smooth muscle, the appearance of foam cells and the accumulation of the fibrous tissue. Hypercholesterolemia can therefore result in very serious cardiovascular pathologies such as infarction, peripheral vascular disease, stroke, sudden death, cardiac decompensation, cerebral vascular accidents and the like.

The cholesterol is carried in the blood by various lipoproteins including the very low-density lipoprotein (VLDL), the low-density lipoproteins (LDL) and the high-density lipoproteins (HDL). The VLDL is synthesized in the liver and is converted to LDL in the blood, which makes it possible to supply the peripheral tissues with cholesterol. In contrast, the HDL captures cholesterol molecules from the peripheral tissues and transports them to the liver where they are converted to bile acids and excreted. The development of atherosclerosis and the risk of coronary heart disease (CHD) inversely correlate to the levels of HDL in the serum. Gordon et al. (1989) N. Engl. J. Med. 321: 1311; Goldbourt et al. (1997) Thromb Vasc. Biol. 17: 107. Low HDL cholesterols often occur in the context of central obesity, diabetes and other features of the metabolic syndrome. Goldbourt et al., supra. It has been suggested that low HDL cholesterol levels are associated with an increased risk of CHD, while high concentrations of HDL have a protective effect against the development of premature atherosclerosis. Gordon et al. (1986) Circulation 74: 1217. Studies demonstrated that the risk for developing clinical atherosclerosis in men drops 2-3% with every 1 mg/dL increase in the concentration of HDL in plasma. Gordon et al. (1989) N. Engl. J. Med. 321: 1311. It has been established that concentrations of LDL cholesterol can be reduced by treatment with statins, inhibitors of the cholesterols biosynthesis enzyme 3-hydroxyl-3-methylglutary Coenzyme A reductase and thereby this treatment has been used as a successful approach for reducing the risk for atherosclerosis where the primary indication is high LDL level. However, it remains unclear whether statins are beneficial for patients whose primary lipid abnormality is low HDL cholesterol.

Lecithin-cholesterol acyltransferase (LCAT) is an enzyme which catalyses the esterification of free cholesterol by the transfer of an acyl group from phosphatidylcholine onto 3-hydroxyl group of the cholesterol, forming cholesteryl ester and lysophosphatidylcholine. McLean et al. (1986) Proc. Natl. Acad. Sci. 83: 2335 and McLean et al. (1986) Nucleic Acids Res. 14(23): 9397. LCAT is synthesized in the liver and secreted into the plasma, where it is combined with HDL, called anti-atherogenic lipoproteins. These HDL particles have the capacity to accept the excess cholesterol, which is then esterified by LCAT in the HDL particles. The cholesteryl ester molecules in the HDL particles are either transported to the liver directly through SR-BI receptor, or transferred to apoB-containing lipoproteins, including very low density lipoproteins (VLDL) and LDL, mediated by CETP, and then transported to the liver through LDL-receptor pathway. This mechanism, called reverse cholesterol transport (Glomset (1968) J. Lipid Res. 9:155), allows the removal of excess cholesterol from the body, and therefore is involved in the prevention of atherogenesis. LCAT plays a key role in this process by creating a gradient of free cholesterol between the plasma membranes and the circulating lipoproteins.

This invention provides modified LCAT proteins with increased enzymatic activity and/or stability and methods for treatment of coronary heart disease, atherosclerosis, inflammatory disorders and disorders associated with thrombosis using these modified LCAT proteins.

SUMMARY OF THE INVENTION

Provided herein are modified LCAT proteins comprising an amino acid substitution in a wild type LCAT protein amino acid sequence. In one aspect, the modified LCAT protein is more enzymatically active than the wild type LCAT protein from which the modified LCAT protein is derived. In another aspect, the modified LCAT protein increases levels of high density lipoprotein (HDL) to an extent that is greater than the wild type LCAT protein from which the modified LCAT protein is derived. In another aspect, the modified LCAT protein is more stable in vivo, or less immunogenic than the wild type protein from which it was derived.

In one embodiment, the modified LCAT protein comprises an amino acid residue substitution at position 31 in SEQ ID NO: 1 or at a position in an ortholog wild-type LCAT protein amino acid sequence corresponding to position 31 in SEQ ID NO: 1 is substituted. In various aspects, the modified LCAT protein is derived from wild type human, rabbit, monkey, hamster mouse or rat LCAT protein.

In another embodiment, the modified LCAT protein is derived from a wild type LCAT amino acid sequence set out in SEQ ID NO: 1, and includes a substitution at position F1, L3, L4, N5, L7, C31, N384 or E416. In various aspects, the substitution is F1A, F1G, F1I, F1L, F1M, F1P, F1V, F1C, F1Y, F1T, F1Q, F1N, F1H or F1D. In other aspects, the substitution is L31, L3F, L3C, L3W or L3Y. In still other aspects, the substitution is L4A, L4I, L4M, L4F, L4V, L4W, L4Y, L4T, L4Q or L4R. In still other aspects, the substitution is N5A, N5M, N5H, N5K, N5D or N5E. In yet other aspects, the substitution is L7M, L7F or L7E. In other aspects, the substitution is C31A, C31I, C31M, C31F, C31V, C31W, C31Y, C31T, C31R or C31H. In still other aspects, the substitution is N384C, N384Q or E416C.

In other embodiments, the modified LCAT protein comprising a substitution at position C31 in SEQ ID NO: 1 and a substitution at amino acid residue position F1, L4, N5, V28, P29, G30, L32, G33 or N34. In various aspects, the substitution is F1A, L4F, N5E, N5Q, N5D, N5A, V28A, V28I, V28C, V28T, V28R, P29G, P29F, P29T, G30A, G30I, L32A, L32I, L32M, L32F, L32C, L32W, L32Y, L32T, L32S, L32N, L32H, L32E, G33I, G33M, G33F, G33S, G33H, N34A, N34C, N34S or N34R. In other aspects, the substitution at position C31 is C31A, C31I, C31M, C31F, C31V, C31W, C31Y, C31T, C31R or C31H. In one aspect, the modified LCAT protein comprises a C31Y substitution and an addition substitution F1, L4, L32, or N34, and in certain aspects, these substitutions are F1S, F1W, L4M, L4K, N34S, L32F, or L32H.

In still other embodiments a modified LCAT protein described herein further includes a vehicle, and in various aspects, the vehicle is an immunoglobulin constant (Fc) region or a water soluble polymer, or more specifically, a water soluble polymer that is polyethylene glycol.

In other embodiments, a modified LCAT as provided herein includes a region of wild type LCAT protein amino terminal amino acid sequence that is duplicated and covalently attached to a terminus of the modified LCAT protein. In one aspect, the region of wild type LCAT protein amino terminal amino acid sequence is 10 to 15 amino acids in length. In other aspects, the region of the wild type LCAT protein amino acid sequence is duplicated and covalently attached to the amino terminus of the modified LCAT protein, the carboxy terminus of the modified LCAT protein, or both.

Also provided are pharmaceutical compositions comprising a modified LCAT protein as provided here and a pharmaceutically acceptable carrier.

Method of treating an LCAT-related disorder are also provided comprising the step of administering an amount of a modified LCAT protein provided herein in an amount effective to treat said disorder. In different embodiments, the modified LCAT is administered intravenously or administered by bolus. In various aspects in the methods of treatment, the LCAT-related disorder is atherosclerosis, inflammation, thrombosis, coronary heart disease, high blood pressure, LCAT deficiency syndrome, Alzheimer's disease, corneal opacity, metabolic syndrome, dyslipidemia, myocardial infarction, stroke, critical limb ischemia, and/or angina.

Also provided is a method for increasing HDL cholesterol in a subject comprising the step of administering to the subject a therapeutically effective amount of a modified LCAT protein provided herein.

The invention further provides a method for preventing accumulation of cholesterol in a subject comprising administering a therapeutically effective amount of a modified LCAT protein as provide herein.

DESCRIPTION OF THE DRAWINGS

FIG. 1A-1J provides Genbank Accession numbers for wild type LCAT proteins amenable for producing modified LCAT proteins.

DETAILED DESCRIPTION OF THE INVENTION

I. Definitions

The term "LCAT" or "lecithin-cholesterol acyltransferase," as used herein, refers to a wild type glycoprotein enzyme that catalyzes the synthesis of cholesterol esters and lysolecithin from phosphatidylcholine and unesterified cholesterol present in lipoproteins. This enzyme is produced primarily by the liver and circulates in blood reversibly bound to lipoproteins. Human LCAT (SEQ ID NO: 1; Genbank Accession No. AAB34898) has a polypeptide mass of 49 kDa, or around 67 kDa with added carbohydrate mass. Various LCAT amino acid sequences for obtaining a modified LCAT protein useful in this invention are represented in FIG. 1A-1J.

```
Human LCAT (SEQ ID NO: 1; Genbank Accession No.
AAB34898)
FWLLNVLFPP HTTPKAELSN HTRPVILVPG CLGNQLEAKL

DKPDVVNWMC YRKTEDFFTI WLDLNMFLCL GVDCWIDNTR

VVYNRSSGLV SNAPGVQIRV PGFGKTYSVE YLDSSKLAGY

LHTLVQNLVN NGYVRDETVR AAPYDWRLEP GQQEEYYRKL

AGLVEEMHAA YGKPVFLIGH SLGCLHLLYF LLRQPQAWKD

RFIDGFISLG APWGGSIKPM LVLASGDNQG IPIMSSIKLK

EEQRITTTSP WMFPSRMAWP EDHVFISTPS FNYTGRDFQR

FFADLHFEEG WYMWLQSRDL LAGLPAPGVE VYCLYGVGLP

TPRTYIYDHG FPYTDPVGVL YEDGDDTVAT RSTELCGLWQ

GRQPQPVHLL PLHGIQHLNM VFSNLTLEHI NAILLGAYRQ

GPPASPTASP EPPPPE
```

The term "modified LCAT" refers to lecithin-cholesterol acyltransferase as defined above, wherein one or more amino acids in the wild type LCAT protein is substituted with another amino acid, or one or more amino acids is added to the either end or the middle of the wildtype LCAT from which the modified LCAT protein is derived. Modified LCAT proteins contemplated have improved pharmacokinetic properties compared to the wild type LCAT protein from which the modified LCAT protein is derived. More specifically, a modified LCAT protein has either (i) increased enzymatic activity compared to wild type LCAT protein from which the modified LCAT protein is derived as measured in the same in vitro assay conditions, (ii) increased ability to increase HDL levels in vivo compared to wild type LCAT protein from which the modified LCAT protein is derived, (iii) increased plasma stability or half-life time, i.e., increased circulatory half-life, compared to plasma stability of wild type LCAT protein from which the modified LCAT protein is derived, and/or (iv) decreased immunogenicity (i.e. evokes less of an immune response) compared to wild type LCAT protein from which the modified LCAT protein is derived. Assays for measuring LCAT enzyme activity include, e.g., use of apoAI-liposome assay and use of plasma LCAT activity assay, which determine cholesterol esterification rate in an artificial system and in a physiologically relevant system, respectively. Assays for measuring LCAT stability in vivo include ELISA, which determines the half-life of recombinant LCAT protein in the blood after LCAT protein administration. Biologically active fragments of a modified LCAT protein are contemplated to the extent that the fragment includes the amino acid change(s) introduced into the wild-type LCAT amino acid sequence.

The terms "derivatizing," "derivative" or "derivatized" comprise processes and resulting modified LCAT proteins in which, for example and without limitation, (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —NRR$_1$, NRC(O)R$_1$, —NRC(O)OR$_1$, —NRS(O)$_2$R$_1$, —NHC(O)NHR, a succinimide group, or substituted or unsubstituted benzyloxycarbonyl-NH—, wherein R and $R_1$ and the ring substituents are as defined hereinafter; (5) the C-terminus is replaced by —C(O)$R_2$ or —NR$_3$R$_4$ wherein $R_2$, $R_3$ and $R_4$ are as defined hereinafter; and (6) compounds in which individual amino acid moieties are modified through treatment with agents capable of reacting with selected side chains or terminal residues. Derivatizing a modified LCAT protein does not further change the modified LCAT protein amino acid sequence, except to the extent that derivitization includes addition of one or more amino acid resides at the carboxy terminus of the modified LCAT protein amino acid sequence, the amino terminus of the modified LCAT protein amino acid sequence, or both the carboxy terminus and the amino terminus of the modified LCAT protein amino acid sequence. In addition, a modified LCAT protein can be derivatized with a side chain modification to an amino acid residue, with the proviso that the side chain modification of cysteine at position 31 in the wild type human LCAT sequence, and corresponding cysteine residues in human homologs and orthologous proteins as identified by amino acid sequence alignment, including necessary gaps, are excluded from the scope of the invention. Further, it will be understood that whenever "modified LCAT protein" is mentioned herein, a modified LCAT protein derivative is also contemplated for that aspect of the invention described.

The term "pharmacologically active" means that a substance so described is determined to have activity that affects a medical parameter (e.g., blood pressure, blood cell count, cholesterol level) or disease state (e.g., atherosclerosis, inflammatory and thrombosis disorders).

The term "physiologically acceptable salts" comprises any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

"Substantially homogenous" as used herein with reference to a preparation of the invention means that the preparation includes a single species of a therapeutic compound detectable in the preparation of total therapeutic molecules in the preparation, unless otherwise stated at a specific percentage of total therapeutic molecules. In general, a substantially homogenous preparation is homogenous enough to display the advantages of a homogenous preparation, e.g., ease in clinical application in predictability of lot to lot pharmacokinetics.

"Bioefficacy" refers to the capacity to produce a desired biological effect. Bioefficacy of different compounds, or different dosages of the same compound, or different administrations of the same compound are generally normalized to the amount of compound(s) to permit appropriate comparison.

"Atherosclerosis" refers to a condition characterized by the hardening and/or narrowing of the arteries caused by the buildup of athermatous plaque inside the arterial walls. The atheromatous plaque is divided in three components, (1) the atheroma, a nodular accumulation of a soft flaky material at the center of large plaques, composed of macrophages nearest the lumen of the artery; (2) underlying areas of cholesterol crystals; (3) calcification at the outer base of more advanced lesions. Indicators of atherosclerosis include, for example, the development of plaques in the arteries, their calcification, the extent of which can be determined by Sudan IV staining, or the development of foam cells in arteries. The narrowing of the arteries can be determined by coronary angioplasty, ultrafast CT, or ultrasound.

"Inflammation" or "inflammatory disorder" refers to a localized, protective response elicited by injury or destruction of tissues, which serves to destroy, dilute or wall off (sequester) both the injurious agent and the injured tissue. The term "inflammatory disease" or "inflammatory condition" as used herein, means any disease in which an excessive or unregulated inflammatory response leads to excessive inflammatory symptoms, host tissue damage, or loss of tissue function. Additionally, the term "autoimmune disease," as used herein, means any group of disorders in which tissue injury is associated with humoral or cell-mediated responses to the body's own constituents. The term "allergic disease," as used herein, means any symptoms, tissue damage, or loss of tissue function resulting from allergy. The term "arthritic disease," as used herein, means any of a large family of diseases that are characterized by inflammatory lesions of the joints attributable to a variety of etiologies. The term "dermatitis," as used herein, means any of a large family of diseases of the skin that are characterized by inflammation of the skin attributable to a variety of etiologies. The term "transplant rejection," as used herein, means any immune reaction directed against grafted tissue (including organ and cell (e.g., bone marrow)), characterized by a loss of function of the grafted and surrounding tissues, pain, swelling, leukocytosis and thrombocytopenia.

"Thrombosis" and "thrombosis-related disorder" refer to abnormal thrombus formation that causes obstruction of blood vessels and conditions associated with such obstruction. Blood vessels operate under significant shear stresses that are a function of blood flow shear rate. Frequently, there is damage to small blood vessels and capillaries. When these vessels are damaged, hemostasis is triggered to stop the bleeding. Under typical circumstances, such an injury is dealt with through a sequence of events commonly referred to as the "thrombus formation". Thrombus formation is dependent upon platelet adhesion, activation and aggregation and the coagulation cascade that culminates in the conversion of soluble fibrinogen to insoluble fibrin clot. Thrombus formation at site of wound prevents extravasation of blood components. Subsequently, wound healing and clot dissolution occurs and blood vessel integrity and flow is restored.

The term "HDL" refers to the high-density lipoproteins.

The term "LDL", as used herein, means the low-density lipoproteins.

The term "VLDL" refers to the very low density lipoproteins.

The term "treatment" or "treating" includes the administration to a subject in need of a pharmacologically active amount of a modified LCAT protein of the invention which will inhibit, decrease or reverse development of, for example, a pathological atherosclerosis, inflammatory disorder, or thrombosis-related disorder. In another aspect, treatment as used herein means the administration, to a subject in need, of an amount of a compound of the invention, which, with respect to atherosclerosis, will increase HDL cholesterol levels. "Inhibiting," in connection with inhibiting atherosclerosis, is intended to mean preventing, retarding, stabilizing, or reversing formation or growth of atheromatous plaques, inflammatory disorder, or thrombosis-related disorder. Treatment of diseases and disorders herein is intended to also include therapeutic administration of a modified LCAT protein of the invention (or a pharmaceutical salt, derivative or prodrug thereof) or a pharmaceutical composition containing the modified LCAT protein to a subject believed to be in need of treatment for diseases and disorders, such as, for example, inflammatory disorders, thrombosis disorders, coronary heart disease, high blood pressure, LCAT deficiency syndrome, Alzheimer's disease, corneal opacity, metabolic syndrome, dyslipidemia, myocardial infarction, stroke, critical limb ischemia, angina and the like. Treatment also encompasses administration of the modified LCAT protein or pharmaceutical composition to subjects not having been diagnosed as having a need thereof, i.e., prophylactic administration to the subject, for prevention of a condition or disorder. Generally, the subject is initially diagnosed by a licensed physician and/or authorized medical practitioner, and a regimen for prophylactic and/or therapeutic (acute or chronic) treatment via administration of the modified LCAT protein(s) or compositions of the invention is suggested, recommended or prescribed.

The phrase "therapeutically effective amount" is the amount of the compound of the invention that will achieve the goal of improvement in disorder severity and the frequency of incidence. The improvement in disorder severity includes, for example with respect to atherosclerosis, prevention of accumulation of cholesterol in vessel walls increasing of blood levels of HDL cholesterol, the reversal of atherosclerosis, as well as slowing down the progression of atherosclerosis, prevention or treatment of inflammatory disorders, and prevention or treatment of thrombosis-relating conditions.

As used herein, the term "subject" is intended to mean a human or other mammal, exhibiting, or at risk of developing, atherosclerosis, an inflammatory disorder or a thrombosis-related disorder. Such an individual can have, or be at risk of developing, for example, conditions such as inflammation, thrombosis, coronary heart disease, high blood pressure, LCAT deficiency syndrome, Alzheimer's disease, corneal opacity, metabolic syndrome, dyslipidemia, myocardial infarction, stroke, critical limb ischemia, angina and the like. The prognostic and clinical indications of these conditions are known in the art.

II. Modified LCAT Proteins

A. Assays

Assays for determining LCAT enzyme activity, plasma stability (enzyme half-life in the plasma) or the plasma LCAT protein levels are known in the art. Absolute LCAT activity in the serum and endogenous cholesterol esterification rate can be determined as described, e.g., in Albers J. et al. (1986) Methods in Enzymol. 129: 763-783; Dobiasova M. et al. (1983) Adv. Lipid Res. 20: 107-194. In one aspect, LCAT activity can be determined by measuring the conversion of radiolabeled cholesterol to cholesterol ester after incubation of LCAT and radiolabeled LCAT substrates containing Apo A-I. Cholesterol esterification rate (CER, nmol CE/mL per hour) can be measured by determining the rate of conversion of labeled cholesterol to cholesteryl ester after incubation of plasma that is radiolabeled with a trace amount of radioactive cholesterol by equilibration with a [$^{14}$C] cholesterol-albumin mixture at 4° C. The endogenous cholesterol esterification rate (as determined with plasma LCAT activity assay) reflects not only on mass of LCAT, but also the nature and amount of LCAT substrate and cofactor present in the serum, and therefore provides a better measure of the therapeutic LCAT activity.

Assays for measuring LCAT stability (half-life) in the blood and plasma LCAT protein concentration are also known in art. After administration, recombinant LCAT protein levels in the plasma can be determined by using ELISA described by J R Crowther: ELISA theory and practice, methods in molecular Biology Volume 42). Reagents for measuring LCAT stability and protein concentration include anti-LCAT antibodies, which are commercially available from several vendors. Examples of use of this assay to determine activity and/or stability of the modified LCAT are given below.

B. Amino Acid Modifications

Modified LCAT proteins are provided comprising an amino acid substitution in a wild type LCAT protein amino acid sequence. Because the amino acid sequence in a wild type LCAT protein is modified through substitution of one or more amino acids, the modified LCAT protein is, in one aspect, a non-naturally-occurring protein. Modified LCAT proteins are derived from any wild type LCAT protein, with exemplary wild type LCAT proteins set out in FIG. 1A-1J.

For aspects of the invention that include treatment of human conditions that arise from LCAT-related disorders, the invention provides modified LCAT proteins wherein a human LCAT protein is modified to include one or more amino acid substitutions, or one or more amino acid addition, and in one aspect, the wild type human LCAT amino acid sequence is set out in SEQ ID NO: 1. In discussion of specific amino acids in the human LCAT protein sequence set out in SEQ ID NO: 1, it will be understood by the worker of ordinary skill in the art that the same or similar modification at the same or corresponding amino acid residue in other human LCAT amino acid sequences (i.e., allelic variants or other naturally-occurring LCAT sequences) or in orthologous LCAT amino acid sequences are contemplated and embraced. With respect to SEQ ID NO: 1, amino acid substitutions are contemplated at (using single letter amino acid designations followed by position in the protein sequence, i.e., "F1" indicates phenylalanine at position 1 in SEQ ID NO: 1: F1, W2, L3, L4, N5, V6, L7, F8, P9, P10, H11, T12, T13, P14, K15, A16, E17, L18, S19, N20, H21, T22, R23, P24, V25, I26, L27, V28, P29, G30, C31, L32, G33, N34, Q35, L36, E37, A38, K39, L40, D41, K42, P43, D44, V45, V46, N47, W48, M49, C50, Y51, R52, K53, T54, E55, D56, F57, F58, T59, I60, W61, L62, D63, L64, N65, M66, F67, L68, C69, L70, G71, V72, D73, C74, W75, I76, D77, N78, T79, R80, V81, V82, Y83, N84, R85, S86, S87, G88, L89, V90, S91, N92, A93, P94, G95, V96, Q97, I98, R99, V100, P101, G102, F103, G104, K105, T106, Y107, S108, V109, E110, Y111, L112, D113, S114, S115, K116, L117, A118, G119, Y120, L121, H122, T123, L124, V125, Q126, N127, L128, V129, N130, N131, G132, Y133, V134, R135, D136, E137, T138, V139, R140, A141, A142, P143, Y144, D145, W146, R147, L148, E149, P150, G151, Q152, Q153, E154, E155, Y156, Y157, R158, K159, L160, A161, G162, L163, V164, E165, E166, M167, H168, A169, A170, Y171, G172, K173, P174, V175, F176, L177, I178, G179, H180, S181, L182, G183, C184, L185, H186, L187, L188, Y189, F190, L191, L192, R193, Q194, P195, Q196, A197, W198, K199, D200, R201, F202, I203, D204, G205, F206, I207, S208, L209, G210, A211, P212, W213, G214, G215, S216, I217, K218, P219, M220, L221, V222, L223, A224, S225, G226, D227, N228, Q229, G230, I231, P232, I233, M234, S235, S236, I237, K238, L239, K240, E241, E242, Q243, R244, I245, T246, T247, T248, S249, P250, W251, M252, F253, P254, S255, R256, M257, A258, W259, P260, E261, D262, H263, V264, F265, I266, S267, T268, P269, S270, F271, N272, Y273, T274, G275, R276, D277, F278, Q279, R280, F281, F282, A283, D284, L285, H286, F287, E288, E289, G290, W291, Y292, M293, W294, L295, Q296, S297, R298, D299, L300, L301, A302, G303, L304, P305, A306, P307, G308, V309, E310, V311, Y312, C313, L314, Y315, G316, V317, G318, L319, P320, T321, P322, R323, T324, Y325, I326, Y327, D328, H329, G330, F331, P332, Y333, T334, D335, P336, V337, G338, V339, L340, Y341, E342, D343, G344, D345, D346, T347, V348, A349, T350, R351, S352, T353, E354, L355, C356, G357, L358, W359, Q360, G361, R362, Q363, P364, Q365, P366, V367, H368, L369, L370, P371, L372, H373, G374, I375, Q376, H377, L378, N379, M380, V381, F382, S383, N384, L385, T386, L387, E388. H389, I390, N391, A392, I393, L394, L395, G396, A397, Y398, R399, Q400, G401, P402, P403, A404, S405, P406, T407, A408, S409, P410, E411, P412, P413, P414, P415 and/or E 416. Amino acids at one or more of these positions are substituted with any naturally-occurring or non-naturally-occurring amino acids. For example and without limitation, the modified LCAT comprises a C31Y substitution and a substitution at one or more of amino acid residues F1, L4, L32, and N34. In one aspect, this second substitution is F1S, F1W, L4M, L4K, N34S, L32F, and/or L32H.

In various aspects, particular substitutions are provided. For example, and without limitation, an aliphatic amino acid residue (G, A, V, L, or I) is substituted with another aliphatic, an aromatic amino acid residue (F, Y, or W) is substituted with another aromatic residue, an aliphatic hydroxyl side chain residue (S or T) is replaced with another aliphatic hydroxyl side chain residue, a basic residue (K, R, or H) is replaced with another basic amino acid residue, an acidic residue (D or E) is replaced with another acidic amino acid residue, an amide side chain residue (N or Q) is replaced with another amide side chain residue, a hydrophobic residue (norleucine, M, A, V, L, or I) is replaced with another hydrophobic residue, a neutral amino acid residue (C, S, T, N, or Q) is replaced with another neutral residue, a residue that influences chain orientation (G or P) is replaced with another residue that influences chain orientation, and/or a sulfur-containing side chain residue (C or M) is replaced with another sulfur-containing side chain residue.

In other aspects, also without limitation, conservative substitutions are introduced into a wild type LCAT amino acid sequence.

TABLE 1

| Original Residue | Exemplary Conservative Substitutions |
|---|---|
| A | G, S |
| R | K |
| N | Q, H |
| D | E |
| C | S |
| Q | N |
| E | D |
| G | A, P |
| H | N, Q |
| I | L, V |
| L | I, V |
| K | R, Q, E |
| M | L, Y, I |
| F | M, L, Y |
| S | T |
| T | S |
| W | Y |
| Tyr | W, F |
| Val | I, L |

Still other substitutions contemplated include, also without limitation, those set out in Table 2 below.

TABLE 2

| Original Residue | Exemplary Substitutions |
|---|---|
| A | V, L, I |
| R | K, Q, N |
| N | Q |
| D | E |
| C | S, A |
| Q | N |
| E | D |

TABLE 2-continued

| Original Residue | Exemplary Substitutions |
|---|---|
| G | P, A |
| H | N, Q, K, R |
| I | L, V, M, A, F, Norleucine |
| L | Norleucine, I, V, M, A, F |
| K | R, 1,4 Diamino-butyric Acid, Q, N |
| M | L, F, I |
| F | L, V, I, A, Y |
| P | A |
| S | T, A, C |
| T | S |
| W | Y, F |
| Y | W, F, T, S |
| V | I, M, L, F, A, Norleucine |

C. Derivatives

In addition to modified LCAT proteins described above, it is contemplated that other "derivatives" of modified LCAT proteins may be substituted for a modified LCAT protein described above. Such derivatives may improve the solubility, absorption, biological half life, and the like of the compounds. The moieties may alternatively eliminate or attenuate any undesirable side-effect of the compounds and the like.

Such derivatives of modified LCAT proteins include those in which:

1. The modified LCAT proteins or some portion thereof is cyclic. For example, the peptide portion may be modified to contain two or more cysteine residues (e.g., in the linker), which could cyclize by disulfide bond formation.

2. The modified LCAT protein is cross-linked or is rendered capable of cross-linking between molecules. For example, the peptide portion may be modified to contain one cysteine residue and thereby be able to form an intermolecular disulfide bond with a like molecule. The protein may also be cross-linked through its C-terminus.

3. One or more peptidyl [—C(O)NR—] linkages (bonds) is replaced by a non-peptidyl linkage. Exemplary non-peptidyl linkages are —$CH_2$-carbamate [—$CH_2$—OC(O)NR—], phosphonate, —$CH_2$-sulfonamide [—$CH_2$—S(O)$_2$NR—], urea [—NHC(O)NH—], —$CH_2$-secondary amine, and alkylated peptide [—C(O)N$R_6$— wherein $R_6$ is lower alkyl].

4. The N-terminus is derivatized. Typically, the N-terminus may be acylated or modified to a substituted amine. Exemplary N-terminal derivative groups include —NR$R^1$ (other than —NH$_2$), —NRC(O)$R^1$, —NRC(O)O$R^1$, —NRS(O)$_2R^1$, —NHC(O)NH$R^1$, succinimide, or benzyloxycarbonyl —NH—(CBZ—NH—), wherein R and $R^1$ are each independently hydrogen or lower alkyl with the proviso that R and $R^1$ are not both hydrogen and wherein the phenyl ring may be substituted with 1 to 3 substituents selected from the group consisting of $C_1$-$C_4$ alkyl, $C_1$-$C_4$ alkoxy, chloro, and bromo; to a succinimide group; to a benzyloxycarbonyl-NH— (CBZ—NH—) group; and peptides wherein the free C terminus is derivatized to —C(O)$R_2$ where $R_2$ is selected from the group consisting of lower alkoxy and —N$R^3R^4$ where $R^3$ and $R^4$ are independently selected from the group consisting of hydrogen and lower alkyl. By "lower" is meant a group having from 1 to 6 carbon atoms.

5. The C-terminus is derivatized. Typically, the C-terminus is esterified or amidated. For example, one may use methods described in the art to add (NH—$CH_2$—$CH_2$—NH$_2$)$_2$ to compounds of this invention at the C-terminus. Likewise, one may use methods described in the art to add —NH$_2$ to compounds of this invention at the C-terminus. Exemplary C-terminal derivative groups include, for example, —C(O)$R_2$ wherein $R^2$ is lower alkoxy or —$NR^3R^4$ wherein $R^3$ and $R^4$ are independently hydrogen or $C_1$-$C_8$ alkyl (or $C_1$-$C_4$ alkyl).

6. A disulfide bond is replaced with another, for example, more stable, cross-linking moiety (e.g., an alkylene). See, e.g., Bhatnagar et al. (1996), J. Med. Chem. 39: 3814-9; Alberts et al. (1993) Thirteenth Am. Pep. Symp., 357-9.

7. One or more individual amino acid residues is modified. Various derivatizing agents are known to react specifically with selected side chains or terminal residues, as described in detail below.

Additionally, modifications of individual amino acids may be introduced into the modified LCAT amino acid sequence by reacting targeted amino acid residues of the protein with an organic derivatizing agent that is capable of reacting with selected side chains or terminal residues. The following are exemplary.

Lysinyl and amino terminal residues may be reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizole and tetranitromethane may be used to form O-acetyl tyrosyl species and 3-nitro derivatives, respectively.

Carboxyl side groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues are frequently deamidated to the corresponding glutamyl and aspartyl residues. Alternatively, these residues may be deamidated under mildly acidic conditions. Either form of these residues falls within the scope of this invention.

Cysteinyl residues at a position other than residue 31 can be replaced by amino acid residues or other moieties either to eliminate disulfide bonding or, conversely, to stabilize crosslinking. See, e.g., Bhatnagar et al. (1996), J. Med. Chem. 39: 3814-9.

Derivatization with bifunctional agents is useful for crosslinking the peptides or their functional derivatives to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for protein immobilization.

Other possible modifications include hydroxylation of proline and lysine, phosphorylation of hydroxyl groups of seryl or threonyl residues, oxidation of the sulfur atom in cysteine, methylation of the alpha-amino groups of lysine, arginine, and histidine side chains (Creighton, T. E., Proteins: Structure and Molecule Properties, W.H. Freeman & Co., San Francisco, pp. 79-86 (1983)), acetylation of the N-terminal amine, and, in some instances, amidation of the C-terminal carboxyl groups.

Such derivatized moieties preferably improve one or more characteristics including enzymatic activity, solubility, absorption, biological half life, and the like of the inventive compounds. Alternatively, derivatized moieties result in compounds that have the same, or essentially the same, characteristics and/or properties of the compound that is not derivatized. The moieties may alternatively eliminate or attenuate any undesirable side effect of the compounds and the like.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Modified LCAT proteins of the present invention may be changed at the DNA level, as well. The DNA sequence of any portion of the compound may be changed to codons more compatible with the chosen host cell. For *E. coli*, which is the host cell in one aspect, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Another set of useful derivatives are the above-described molecules conjugated to toxins, tracers, or radioisotopes. Such conjugation is especially useful for molecules comprising peptide sequences that bind to tumor cells or pathogens. Such molecules may be used as therapeutic agents or as an aid to surgery (e.g., radioimmunoguided surgery or RIGS) or as diagnostic agents (e.g., radioimmunodiagnostics or RID).

As therapeutic agents, these conjugated derivatives possess a number of advantages. They facilitate use of toxins and radioisotopes that would be toxic if administered without the specific binding provided by the peptide sequence. They also can reduce the side-effects that attend the use of radiation and chemotherapy by facilitating lower effective doses of the conjugation partner.

Useful conjugation partners include:
- radioisotopes, such as $^{90}$Yttrium, $^{131}$Iodine, $^{225}$Actinium, and $^{213}$Bismuth;
- ricin A toxin, microbially derived toxins such as *Pseudomonas* endotoxin (e.g., PE38, PE40), and the like;
- partner molecules in capture systems (see below);
- biotin, streptavidin (useful as either partner molecules in capture systems or as tracers, especially for diagnostic use); and
- cytotoxic agents (e.g., doxorubicin).

One useful adaptation of these conjugated derivatives is use in a capture system. In such a system, the molecule of the present invention would comprise a benign capture molecule. This capture molecule would be able to specifically bind to a separate effector molecule comprising, for example, a toxin or radioisotope. Both the vehicle-conjugated molecule and the effector molecule would be administered to the patient. In such a system, the effector molecule would have a short half-life except when bound to the vehicle-conjugated capture molecule, thus minimizing any toxic side-effects. The vehicle-conjugated molecule would have a relatively long half-life but would be benign and non-toxic. The specific binding portions of both molecules can be part of a known specific binding pair (e.g., biotin, streptavidin) or can result from peptide generation methods such as those described herein.

Such conjugated derivatives may be prepared by methods known in the art. In the case of protein effector molecules (e.g., *Pseudomonas* endotoxin), such molecules can be expressed as fusion proteins from correlative DNA constructs. Radioisotope conjugated derivatives may be prepared, for example, as described for the BEXA antibody (Coulter). Derivatives comprising cytotoxic agents or microbial toxins may be prepared, for example, as described for the BR96 antibody (Bristol-Myers Squibb). Molecules employed in capture systems may be prepared, for example, as described by the patents, patent applications, and publications from NeoRx. Molecules employed for RIGS and RID may be prepared, for example, by the patents, patent applications, and publications from NeoProbe.

D. Vehicle/Carrier Moieties

The compounds of the invention may also be covalently or noncovalently associated with a carrier molecule, such as a linear polymer (e.g., polyethylene glycol, polylysine, dextran, etc.), a branched-chain polymer (see, for example, U.S. Pat. No. 4,289,872; U.S. Pat. No. 5,229,490; WO 93/21259); a lipid; a cholesterol group (such as a steroid); or a carbohydrate or oligosaccharide. Other possible carries include antibody moieties, and in particular constant regions derived from an antibody. Still other possible carriers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers.

1. Immunoglobulin Constant Region Vehicles/Carriers

In one aspect, a modified LCAT protein of the invention includes at least one vehicle attached to the protein through the N-terminus, C-terminus or a side chain of one of the amino acid residues. In one embodiment, an Fc domain is a vehicle. Thus, an Fc domain may be fused to the N or C termini of the peptides or at both the N and C termini. Multiple vehicles, as exemplified herein, may also be used; e.g., an Fc at each terminus or an Fc at a terminus and a PEG group at the other terminus or a side chain.

In various embodiments, the Fc component is either a native Fc or an Fc variant. By way of example and without limitation, the Fc component is an Fc region of the human immunoglobulin IgG1 heavy chain or a biologically active fragment, derivative, or dimer thereof, see Ellison, J. W. et al., Nucleic Acids Res. 10:4071-4079 (1982). It is understood, however, that an Fc region for use in the invention may be derived from an IgG, IgA, IgM, IgE or IgD from any species. Native Fc domains are made up of monomeric polypeptides that may be linked into dimeric or multimeric forms by covalent (i.e., disulfide bonds) and/or non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). One example of a native Fc is a disulfide-bonded dimer resulting from papain digestion of an IgG (see Ellison et al. (1982), Nucleic Acids Res. 10: 4071-9).

In various aspects, Fc sequences contemplated include those known in the art such as, for example, Fc IgG1 (GenBank Accession No. P01857), Fc IgG2 (GenBank Accession No. P01859), Fc IgG3 (GenBank Accession No. P01860), Fc IgG4 (GenBank Accession No. P01861), Fc IgA1 (GenBank Accession No. P01876), Fc IgA2 (GenBank Accession No. P01877), Fc IgD (GenBank Accession No. P01880), Fc IgM (GenBank Accession No. P01871), and Fc IgE (GenBank Accession No. P01854).

Variants, analogs or derivatives of the Fc portion may be constricted by, for example, making various substitutions of residues or sequences. In one aspect, an Fc variant is incorporated which comprises a molecule or sequence that is humanized from a non-human native Fc. Alternately, an Fc variant comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC), each of which is described in detail in U.S. Patent Application No. 20040087778, the disclosure of which is incorporated by reference in its entirety.

Variant (or analog) Fc polypeptide moieties include any insertion variants, wherein one or more amino acid residues supplement an Fc amino acid sequence. Insertions may be located at either or both termini of the protein, or may be positioned within internal regions of the Fc amino acid sequence. Insertion variants, with additional residues at either or both termini, can include for example, fusion proteins and proteins including amino acid tags or labels. For example, the Fc molecule may optionally contain an N-terminal Met, especially when the molecule is expressed recombinantly in a bacterial cell such as *E. coli*.

In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence.

In Fc substitution variants, one or more amino acid residues of an Fc polypeptide are removed and replaced with alternative residues. In one aspect, the substitutions are conservative in nature and conservative substitutions of this type are well known in the art. Alternatively, the invention embraces substitutions that are also non-conservative.

For example, cysteine residues can be deleted or replaced with other amino acids to prevent formation of some or all disulfide crosslinking of the Fc sequences. Each cysteine residue can be removed and/or substituted with other amino acids, such as Ala or Ser. As another example, modifications may also be made to introduce amino acid substitutions to (1) ablate the Fc receptor binding site; (2) ablate the complement (C1q) binding site; and/or to (3) ablate the antibody dependent cell-mediated cytotoxicity (ADCC) site. Such sites are known in the art, and any known substitutions are within the scope of Fc as used herein. For example, see Molecular Immunology, Vol. 29, No. 5, 633-639 (1992) with regard to ADCC sites in IgG1.

Likewise, one or more tyrosine residues can be replaced by phenylalanine residues. In addition, other variant amino acid insertions, deletions and/or substitutions are also contemplated and are within the scope of the present invention. In one aspect, these could be conservative amino acid substitutions. Furthermore, alterations may be in the form of altered amino acids, such as peptidomimetics or D-amino acids.

As noted above, both native Fc and Fc variants are suitable Fc domains for use within the scope of this invention. A native Fc may be extensively modified to form an Fc variant provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*.

3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.

6. Sites are removed that affect binding to Fc receptors other than a salvage receptor. A native Fc may have sites for interaction with certain white blood cells that are not required for the fusion molecules of the present invention and so may be removed.

7. The ADCC site is removed. ADCC sites are known in the art; see, for example, *Molec. Immunol.* 29 (5): 633-9 (1992) with regard to ADCC sites in IgG1. These sites, as well, are not required for the fusion molecules of the present invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

It should be noted that Fc monomers will spontaneously dimerize when the appropriate cysteine residues are present, unless particular conditions are present that prevent dimerization through disulfide bond formation. Even if the cysteine residues that normally form disulfide bonds in the Fc dimer are removed or replaced by other residues, the monomeric chains will generally form a dimer through non-covalent interactions. The term "Fc" herein is used to mean any of these forms: the native monomer, the native dimer (disulfide bond linked), modified dimers (disulfide and/or non-covalently linked), and modified monomers (i.e., derivatives).

Fc sequences may also be derivatized, i.e., bearing modifications other than insertion, deletion, or substitution of amino acid residues. In one aspect, the modifications are covalent in nature, and include for example, chemical bonding with polymers, lipids, other organic, and inorganic moieties. However, non-covalent modifications are also contemplated. Derivatives of the invention may be prepared to increase circulating half-life, or may be designed to improve targeting capacity for the polypeptide to desired cells, tissues, or organs.

It is also possible to use the salvage receptor binding domain of the intact Fc molecule as the Fc part of a compound of the invention, such as described in WO 96/32478, entitled "Altered Polypeptides with Increased Half-Life." Additional members of the class of molecules designated as Fc herein are those that are described in WO 97/34631, entitled "Immunoglobulin-Like Domains with Increased Half-Lives."

2. Water-Soluble Polymer Vehicles

As noted above, polymer vehicles are also contemplated. Various means for attaching chemical moieties useful as vehicles are currently available, see, e.g., International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

Thus, the invention contemplates compounds comprising a water-soluble polymer (WSP). Suitable, clinically acceptable, WSP include without limitation, PEG, polyethylene glycol propionaldehyde, copolymers of ethylene glycol/propylene glycol, monomethoxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly-β-amino acids (either homopolymers or random copolymers), poly(n-vinyl pyrrolidone)polyethylene glycol, propropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof. In fact, any of the forms of PEG that have been used to derivatize other proteins, such as and without limitation mono-(C1-C10) alkoxy- or aryloxy-polyethylene glycol, are provided. Polyethylene glycol propionaldehyde may have advantages in manufacturing due to its stability in water.

The PEG group may be of any convenient molecular weight and may be linear or branched. The average molecular weight of PEG contemplated for use in the invention ranges from about 2 kDa to about 100 kDa, from about 5 kDa to about 50 kDa, from about 5 kDa to about 10 kDa. In another aspect, the PEG moiety has a molecular weight from about 6 kDa to about 25 kDa. PEG groups generally are attached to peptides or proteins via acylation or reductive alkylation through a reactive group on the PEG moiety (e.g., an aldehyde, amino, thiol, or ester group) to a reactive group on the target peptide or protein (e.g., an aldehyde, amino, or ester group). Using methods described herein, a mixture of polymer/peptide conjugate molecules can be prepared, and the advantage provided herein is the ability to select the proportion of polymer/peptide conjugate to include in the mixture. Thus, if desired, a mixture of peptides with various numbers of polymer moieties attached (i.e., zero, one or two) can be prepared with a predetermined proportion of polymer/protein conjugate.

A useful strategy for the PEGylation of synthetic peptides consists of combining, through forming a conjugate linkage in solution, a peptide and a WSP (PEG) moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of WSP which may be used for protein modification. Dextrans are polysaccharide polymers comprised of individual subunits of glucose predominantly linked by $\alpha$1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456. Dextran of about 1 kD to about 20 kD is preferred when dextran is used as a vehicle in accordance with the present invention.

The WSP moiety of the molecule may be branched or unbranched. For therapeutic use of the end-product preparation, the polymer is pharmaceutically acceptable. In general, a desired polymer is selected based on such considerations as whether the polymer conjugate will be used therapeutically, and if so, the desired dosage, circulation time, resistance to proteolysis, and other considerations. In various aspects, the average molecular weight of each WSP is between about 2 kDa and about 100 kDa, between about 5 kDa and about 50 kDa, between about 12 kDa and about 40 kDa and between about 20 kDa and about 35 kDa. In yet another aspect, the molecular weight of each polymer is between about 6 kDa and about 25 kDa. The term "about" as used herein and throughout, indicates that in preparations of a water soluble polymer, some molecules will weigh more, some less, than the stated molecular weight. Generally, the higher the molecular weight or the more branches, the higher the polymer/protein ratio. Other sizes may be used, depending on the desired therapeutic profile including for example, the duration of sustained release; the effects, if any, on biological activity; the ease in handling; the degree or lack of antigenicity and other known effects of a water soluble polymer on a therapeutic protein.

The WSP should be attached to the protein with consideration given to effects on functional or antigenic domains of the peptide or protein. In general, chemical derivitization may be performed under any suitable condition used to react a protein with an activated polymer molecule. Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled.

3. Alternative Vehicles

Alternative vehicles include a protein, polypeptide, peptide, or small molecule (e.g., a peptidomimetic compound) capable of binding to a salvage receptor. For example, one could use as a vehicle a polypeptide as described in U.S. Pat. No. 5,739,277. Peptides could also be selected by phage display for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

III. Production of Modified LCAT Proteins/Methods of Making

A. Polynucleotides

The proteins described herein largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as E. coli sp.), yeast (such as Saccharomyces sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The modified LCAT proteins may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941, 763; Finn et al. (1976), The Proteins (3rd ed.) 2: 105-253; and Erickson et al. (1976), The Proteins (3rd ed.) 2: 257-527. Solid phase synthesis is a contemplated technique of making individual peptides since it is the most cost-effective method of making small peptides.

B. Vectors

For recombinant protein expression, the invention provides a vector encoding a modified LCAT protein which can be expressed in an appropriate host. Such a vector comprises a polynucleotide that encodes a modified LCAT protein, with or without a vehicle modification, operatively linked to appropriate expression control sequences. Methods of effecting operative linking, either before or after the DNA molecule is inserted into the vector, are well known in the art. Expression control sequences include promoters, activators, enhancers, operators, ribosomal binding sites, start signals, stop signals, cap signals, polyadenylation signals, and/or other signals involved with the control of transcription or translation. The worker of skill in the art will appreciate that various combinations of these control sequences can be utilized, depending on, for example, the choice of host cell in which the modified LCAT protein is to be expressed. The resulting vector is transformed into an appropriate host using methods well known in the art.

C. Host Cells

Any of a large number of available and well-known host cells is used to express a modified LCAT protein. Selection of a host is dependent upon a number of factors including, for example and without limitation, compatibility with the chosen expression vector, toxicity of the expressed modified LCAT protein encoded by a transformed polynucleotide, rate of transformation, ease of recovery of the expressed modified LCAT protein, expression characteristics, degree and type of glycosylation, if desired, bio-safety and costs. A balance of these factors must be struck with the understanding that not all host cells may be equally effective for the expression of a particular modified LCAT protein. Depending upon the host cell employed, the modified LCAT expression product may be glycosylated with mammalian or other eukaryotic carbohydrates, or it may be non-glycosylated. The modified LCAT expression product may also include an initial methionine amino acid residue (at amino acid residue position −1) if expressed in, for example, a bacterial host cell. Within these general guidelines, useful host cells include bacteria, yeast and other fungi, insects, plants, mammalian (including human) cells in culture, or other host cells known in the art. Host cells are cultured under conventional fermentation conditions well known in the art to permit expression of the desired compounds and the modified LCAT expression product is purified using techniques also known in the art.

Depending on the host cell utilized to express modified LCAT protein, carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

D. Vehicle modification of a modified LCAT protein

Depending on the method of WSP attachment chosen, the proportion of WSP molecules attached to the target protein molecule will vary, as will their concentrations in the reaction mixture. In general, the optimum ratio (in terms of efficiency of reaction in that there is no excess unreacted protein or polymer) is determined by the molecular weight of the WSP selected. In addition, when using methods that involve non-specific attachment and later purification of a desired species, the ratio may depend on the number of reactive groups (typically amino groups) available.

In general, a WSP is added to a modified LCAT protein via acylation, reductive alkylation, Michael addition, thiol alkylation or other chemoselective conjugation/ligation methods through a reactive group on the WSP (i.e., an aldehydes, amino, ester, thiol, α-haloacetyl, maleimodo or hydrazine group) to a reactive group on the target.

Thus, a process for preparing conjugation derivatives is also contemplated. Thus, one aspect of this invention is a process comprising preparing a modified LCAT agent comprising at least one vehicle by any method described herein or otherwise known in the art. By way of example and without limitation, a reductive alkylation chemical modification procedure method may be utilized. An alternative method for WSP modification is described in Francis et al., in: Stability of protein pharmaceuticals: in vivo pathways of degradation and strategies for protein stabilization (Eds. Ahern., T. and Manning, M. C.) Plenum, N.Y., 1991, is used. In still another aspect, the method described in Delgado et al., "Coupling of PEG to Protein By Activation With Tresyl Chloride, Applications In Immunoaffinity Cell Preparation", In: Fisher et al., eds., Separations Using Aqueous Phase Systems, Applications In Cell Biology and Biotechnology, Plenum Press, N.Y., N.Y., 1989 pp. 211-213, which involves the use of tresyl chloride, which results in no linkage group between the WSP moiety and the modified LCAT protein. This alternative method, however, may be difficult to use to produce therapeutic products as the use of tresyl chloride may produce toxic by-products. In other aspects, attachment of a WSP is effected through use of N-hydroxy succinimidyl esters of carboxymethyl methoxy polyethylene glycol, as well known in the art.

1. Reductive Alkylation

In one aspect, covalent attachment of a WSP to a modified LCAT protein is carried out by reductive alkylation chemical modification procedures as provided herein to selectively modify the N-terminal α-amino group, and testing the resultant product for the desired biological characteristic, such as the biological activity assays provided herein.

Reductive alkylation for attachment of a WSP to a protein or peptide exploits differential reactivity of different types of primary amino groups (e.g., lysine versus the N-terminal) available for derivitization in a particular protein. Under the appropriate reaction conditions, substantially selective derivitization of the protein at the N-terminus with a carbonyl group containing polymer is achieved.

Using reductive alkylation, the reducing agent should be stable in aqueous solution and preferably be able to reduce only the Schiff base formed in the initial process of reductive alkylation. Reducing agents are selected from, and without limitation, sodium borohydride, sodium cyanoborohydride, dimethylamine borate, trimethylamine borate and pyridine borate.

The reaction pH affects the ratio of polymer to protein to be used. In general, if the reaction pH is lower than the pKa of a target reactive group, a larger excess of polymer to protein will be desired. If the pH is higher than the target pKa, the polymer:protein ratio need not be as large (i.e., more reactive groups are available, so fewer polymer molecules are needed).

Accordingly, the reaction is performed in one aspect at a pH which allows one to take advantage of the pKa differences between the ε-amino groups of the lysine residues and that of the α-amino group of the N-terminal residue of the protein. By such selective derivitization, attachment of a water soluble polymer to a protein is controlled; the conjugation with the polymer takes place predominantly at the N-terminus of the protein and no significant modification of other reactive groups, such as the lysine side chain amino groups, occurs.

In one aspect, therefore, methods are provided for covalent attachment of a WSP to a target modified LCAT protein which provide a substantially homogenous preparation of WSP/protein conjugate molecules, in the absence of further extensive purification as is required using other chemical modification chemistries. More specifically, if polyethylene glycol is used, methods described allow for production of an N-terminally PEGylated protein lacking possibly antigenic linkage groups, i.e., the polyethylene glycol moiety is directly coupled to the protein moiety without potentially toxic by-products.

E. Purification of a WSP-Modified Compound

The method of obtaining a substantially homogeneous WSP-LCAT protein preparation is, in one aspect, by purification of a predominantly single species of modified LCAT having an attached WSP moiety from a mixture of modified LCAT species having a number of WSP attachments at various locations in the modified LCAT protein sequence. By way of example, a substantially homogeneous modified LCAT species is first separated by ion exchange chromatography to obtain material having a charge characteristic of a single species (even though other species having the same apparent charge may be present), and then the desired species is separated using size exclusion chromatography. Other methods are reported and contemplated by the invention, includes for example, WO 90/04606, which describes a process for fractionating a mixture of PEG-protein adducts comprising partitioning the PEG/protein adducts in a PEG-containing aqueous biphasic system. Such a system of separation can be modified for use with modified LCAT proteins having other (i.e., non-PEG) attachments.

Thus, one aspect of the present invention is a method for preparing a WSP-modified LCAT conjugate comprised of (a) reacting a modified LCAT protein having more than one amino group with a water soluble polymer moiety under reducing alkylation conditions, at a pH suitable to selectively activate the α-amino group at the amino terminus of the protein moiety so that said water soluble polymer selectively attaches to said α-amino group; and (b) obtaining the reaction product. Optionally, and particularly for a therapeutic product, the reaction products are separated from unreacted moieties.

IV. Pharmaceutical Compositions Comprising Modified LCAT and Methods of Administration While it may be possible to administer compounds of the invention alone, in the methods described, the compound administered is generally present as an active ingredient in a desired dosage unit formulation, such as pharmaceutically acceptable composition containing conventional pharmaceutically acceptable carriers. Thus, in another aspect of the invention, there is provided a pharmaceutical composition comprising a compound of this invention in combination with a pharmaceutically acceptable carrier. Acceptable pharmaceutical carriers generally include diluents, excipients, adjuvants and the like as described herein.

A pharmaceutical composition of the invention may comprise an effective amount of a compound of the invention or an effective dosage amount of a compound of the invention. An effective dosage amount of a compound of the invention includes an amount less than, equal to, or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound may be administered by administering a portion of the composition. "Unit dosage" is defined as a discrete amount of a therapeutic composition dispersed in a suitable carrier. Those of ordinary skill in the art will readily optimize effective dosages and administration regimens as determined by good medical practice and the clinical condition of the individual patient.

The pharmaceutical compositions may generally be prepared by mixing one or more modified LCAT proteins with one or more pharmaceutically acceptable carriers, excipients, binders, adjuvants, diluents, preservatives, solubilizers, emulsifiers and the like, to form a desired administrable formulation to treat or ameliorate a variety of diseases. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

The pharmaceutical compositions may be subjected to conventional pharmaceutical operations such as sterilization and/or may contain conventional adjuvants, such as preservatives, stabilizers, wetting agents, emulsifiers, buffers etc. The pharmaceutically active compounds of this invention can be processed in accordance with conventional methods of pharmacy to produce medicinal agents for administration to patients, including humans and other mammals.

Pharmaceutical compositions can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration (including pulmonary and nasal administration), parenteral administration (including subcutaneous administration), transdermal (topical) administration or by rectal administration, as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (2000); and "Pharmaceutics The Science of Dosage Form Design, $2^{nd}$ Ed. (Aulton, ed.) Churchill Livingstone (2002). The following dosage forms are given by way of example and should not be construed as limiting the invention.

A. Oral Administration

For oral, buccal, and sublingual administration, powders, suspensions, granules, tablets, pills, capsules, gelcaps, troches or lozenges, cachets, pellets and caplets are acceptable as solid dosage (and unit dosage) forms and are described generally in Chapter 89 of Remington's Pharmaceutical Sciences (1990), 18th Ed., Mack Publishing Co. Easton Pa. 18042. Solid dosage forms also include liposomal or proteinoid encapsulation (for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given in Chapter 10 of Marshall, K., Modern Pharmaceutics (1979), edited by G. S. Banker and C. T. Rhodes. In general, the formulation includes the modified LCAT protein, and inert ingredients which allow for protection against the stomach environment, and release of the biologically active material in the intestine.

If necessary, the compounds are chemically modified to enhance bioefficacy of oral delivery. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline as well as other moieties described herein. See also, for example, Abuchowski and Davis, Soluble Polymer-Enzyme Adducts, Enzymes as Drugs (1981), Hocenberg and Roberts, eds., Wiley-Interscience, New York, N.Y., pp 367-83; Newmark, et al. (1982), J. Appl. Biochem. 4: 185-9. Other polymers that could be used are poly-1,3-dioxolane and poly-1,3,6-tioxocane. In one aspect, PEG moieties are provided for pharmaceutical usage, as indicated above.

For oral delivery dosage forms, it is also possible to use a salt of a modified aliphatic amino acid, such as sodium N-(8-[2-hydroxybenzoyl]amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Oral pharmaceutical compositions contemplated can be prepared, for example, by mixing one or more compounds of the instant invention with at least one additive or excipient such as a starch or other additive and tableted, encapsulated or made into other desirable forms for conventional administration. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, and the like may be added for oral or parenteral administration.

More specifically, various aspects of oral pharmaceutical compositions include one or more of the following additives.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

B. Pulmonary Delivery Forms

Also contemplated herein is pulmonary delivery of the present protein (or derivatives thereof). The protein (or derivative) is delivered to the lungs of a mammal while inhaling and traverses across the lung epithelial lining to the blood stream. Other reports of this include Adjei et al., Pharma. Res. (1990) 7: 565-9; Adjei et al. (1990), Internatl. J. Pharmaceutics 63: 135-44 (leuprolide acetate); Braquet et al. (1989), J. Cardiovasc. Pharmacol. 13 (suppl.5): s.143-146 (endothelin-1); Hubbard et al. (1989), Annals Int. Med. 3: 206-12 (α1-antitrypsin); Smith et al. (1989), J. Clin. Invest. 84: 1145-6 (α1-proteinase); Oswein et al. (March 1990), "Aerosolization of Proteins" Proc. Symp. Resp. Drug Delivery II, Keystone, Colorado (recombinant human growth hormone); Debs et al. (1988), J. Immunol. 140: 3482-8 (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 μm (or microns), most preferably 0.5 to 5 μm, for most effective delivery to the distal lung.

Pharmaceutically acceptable carriers for pulmonary delivery include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 ulations may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

D. Parenteral Administration

Injectable dosage forms for parenteral administration generally include aqueous suspensions or oil suspensions, which may be prepared using a suitable dispersant or wetting agent and a suspending agent. Injectable forms may be in solution phase or a powder suitable for reconstitution as a solution. Both are prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

E. Rectal Administration

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

F. Pharmaceutical Formulations and Dosages

The formulations of the invention may be designed to be short-acting, fast-releasing, long-acting, and sustained-releasing as described below. Thus, the pharmaceutical formulations may also be formulated for controlled release or for slow release. The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The dosage regimen for treating LCAT-mediated diseases and other disorders described herein with a modified LCAT protein and/or compositions is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, for example from about 0.1 mg to 10 mg/kg, or from about 0.25 mg to 1 mg/kg are useful for all methods of use disclosed herein. Generally, the daily regimen should be in the range of 0.1-1000 micrograms of the compound per kilogram of body weight, preferably 0.1-150 micrograms per kilogram.

1. Oral Dosages

For oral administration, the pharmaceutical composition may be in the form of, for example, a capsule, a tablet, a suspension, or liquid. The pharmaceutical composition can be made in the form of a dosage unit containing a given amount of the active ingredient. For example, these may contain an amount of active ingredient from about 1 to 2000 mg, for example from about 1 to 500 mg, or from about 5 to 150 mg, or from 10 to 100 mg. A suitable daily dose for a human or other mammal may vary widely depending on the condition of the patient and other factors, but, once again, can be determined using routine methods.

2. Injectable Dosages

The active ingredient may also be administered by injection as a composition with suitable carriers including saline, dextrose, or water. The daily parenteral dosage regimen will be from about 0.1 to about 30 mg/kg of total body weight, such as from about 0.1 to about 10 mg/kg, or from about 0.25 mg to 1 mg/kg.

3. Topical Dosages

Formulations suitable for topical administration include liquid or semi-liquid preparations suitable for penetration through the skin (e.g., liniments, lotions, ointments, creams, or pastes) and drops suitable for administration to the eye, ear, or nose.

A suitable topical dose of active ingredient of a compound of the invention is 0.1 mg to 150 mg administered one to four, for example one or two times daily. For topical administration, the active ingredient may comprise from 0.001% to 10% w/w, e.g., from 1% to 2% by weight of the formulation, although it may comprise as much as 10% w/w, but typically not more than 5% w/w. In one aspect, the concentration is from 0.1% to 1% of the formulation.

G. Administration Regimens

Administration of the compositions can be systemic or local, and may comprise a single site injection or infusion of a therapeutically-effective amount of the modified LCAT protein composition. Any route known to those of skill in the art for the administration of a therapeutic composition of the invention is contemplated including, for example, intravenous, intramuscular, subcutaneous or a catheter for long-term administration. Alternatively, it is contemplated that the therapeutic composition may be delivered to the patient at multiple sites. The multiple administrations may be rendered simultaneously or may be administered over a period of time. In certain cases, it may be beneficial to provide a continuous flow of the therapeutic composition. Additional therapy may be administered on a period basis, for example, daily, weekly, or monthly. In certain embodiments, the modified LCAT polypeptide is provided locally to the site of reperfusion.

V. Methods of Treatment

A. Atherosclerosis, Cardiovascular Disease or an Associated Disease

In one aspect, the methods of treatment of the invention are therapeutic, and compounds and compositions of the invention are administered to a subject already suffering from atherosclerosis, cardiovascular disease or an associated disease. In another aspect, methods of treatment are prophylactic and compounds and compositions are administered to those subjects at risk for developing atherosclerosis. To determine whether a subject is at risk of, for example atherosclerosis, an atherogenic lipoprotein profile can be assessed. For example, a ratio of serum cholesterol to HDLs of 5:1 or above indicates a higher than average risk of developing atherosclerosis. Other factors include a serum cholesterol level of 240 mg/dL or above, an HDL level 35 mg/dL or below, or an LDL level 190 mg/dL or above, a plasma LCAT protein level lower than normal (<5 μg/ml), and a decreased plasma cholesterol esterification rate (<60 nmol/ml/hr).

The amount of modified LCAT protein effective to decrease accumulation of cholesterol depends on several factors, including the species, the manner of administration, the general health of the subject, the desired result (e.g., prophylaxis or therapeutic treatment) and the judgment of the prescribing physician. For example, the practitioner may decide what risk levels for heart disease indicate prophylactic treatment, and what target level of the modified LCAT protein is indicated for the treatment of a person already suffering from atherosclerosis.

In humans, the normal cholesterol esterification rate ranges from about 60 nmol/ml/hr to about 130 nmol/mL per hour. The effective treatment of atherosclerosis in humans can involve administration of the compositions of the invention to achieve a cholesterol esterification rate of about 200 nmol/ml/hr.

The invention provides methods for the treatment, prevention, or management of a cardiovascular disease. As used herein, the term "cardiovascular diseases" refers to diseases of the heart and circulatory system. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarction, cerebral infarction and restenosis, thrombosis, high blood pressure and angina. In one aspect, the invention includes methods of administering the compounds and compositions of the invention for chronic treatment. In another aspect, the invention contemplates acute treatment.

Other diseases which the compositions of the present invention are useful for preventing or treating include LCAT deficiency syndrome, Alzheimer's disease, corneal opacity, metabolic syndrome, dyslipidemia, myocardial infarction, stroke, critical limb ischemia.

B. Inflammatory Conditions

Methods, compounds and compositions of the invention are useful in suppressing inflammatory cell activation. The term "inflammatory cell activation," as used herein, means the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B Lymphocytes, granulocytes, polymorphonuclear leukocytes, mast cells, basophils, eosinophils, dendritic cells, and endothelial cells). It will be appreciated by persons skilled in the art that the activation of one or a combination of these phenotypes in these cells can contribute to the initiation, perpetuation, or exacerbation of an inflammatory condition.

Methods, compounds and compositions of the invention are useful in treating such diseases as arthritic diseases (such as rheumatoid arthritis), osteoarthritis, gouty arthritis, spondylitis, thyroid-associated opthalmopathy, Behcet disease, sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult (acute) respiratory distress syndrome (ARDS), chronic pulmonary inflammatory disease (such as chronic obstructive pulmonary disease), silicosis, pulmonary sarcoidosis, reperfusion injury of the myocardium, brain or extremities, brain or spinal cord injury due to minor trauma, fibrosis including cystic fibrosis, keloid formation, scar tissue formation, atherosclerosis, autoimmune diseases, such as systemic lupus erythematosus (SLE) and transplant rejection disorders (e.g., graft vs. host (GvH) reaction and allograft rejection), chronic glomerulonephritis, inflammatory bowel diseases, such as Crohn's disease and ulcerative colitis, proliferative lymphocytic diseases, such as leukemias (e.g. chronic lymphocytic leukemia; CLL) (see Munoz et al., J. Exp. Med. 172:95-103 (1990); Mentz et al., Blood 88:2172-2182 (1996)), and inflammatory dermatoses, such as atopic dermatitis, psoriasis, or urticaria.

C. Thrombosis-Related Conditions

It is also contemplated that the compounds, compositions and methods of the present invention are used in the treatment of a variety of disorders in which there is a need to prevent or treat thrombosis and subsequent decrease or loss of blood flow. The examples of thrombotic disorders include but not limited to atherosclerosis, myocardial infarction, stroke, and kidney ischemia, and thrombosis in any part of the mammalian body. The composition of the present invention will also be used in the prevention and treatment of microangiopathy in which formation of microthrombi or von Willebrand factor (VWF) binding to platelets causes excessive consumption of platelets and/or VWF leading to subsequent bleeding diathesis. Examples of latter disorders include but not limited to thrombotic thrombocytopenic purpura, type II and platelet type von Willebrand disease (VWD). The compounds or combination therapeutic methods of the present invention inhibit VWF-dependent platelet adhesion and aggregation. The compounds, compositions and methods are also useful in prolonging bleed time in a mammal and as such, are useful as anti-thrombotic agents both in therapeutic and prophylactic methods. As such, these compounds, compositions and methods are useful as anticoagulant agents and/or anti-platelet agents. Further, the present invention provides compounds, compositions and methods for the treatment of thrombosis and other disorders of the cardiovascular circulatory system that require and increase in the flow or reducing blockage of the vessels.

Compounds, compositions and methods are also useful for the treatment of any disorder that is presently treated using anticoagulant therapy. Such disorders include pulmonary embolism, unstable angina, myocardial infarction, deep vein thrombosis, atrial fibrillation with embolization, acute and chronic coagulopathies (disseminated intravascular coagulation), for prevention of clotting in arterial and cardiac surgery, for prophylaxis and treatment of peripheral arterial embolism. The compounds, compositions and methods are also used to treat thrombotic thrombocytopic purpura, other types of microangiopathy that are mediated by spontaneous interaction between VWF and platelets, platelet type or type IIb von Willebrand diseases in which there is an increased binding of VWF to platelets (either caused by a defect in GPIb or in VWF). The compounds, compositions and methods described herein are useful as anti-platelet agents in blood transfusions, extracorporeal circulation, dialysis procedures as well as blood sampling for laboratory procedures. The compounds, compositions and methods are also used to maintain the patency of an indwelling venipucture device that is being used for intermittent injection or infusion therapy or blood sampling. The compounds, compositions and methods are particularly useful in surgical procedures to prevent the formation of blood clots. Such indications are particularly desirable for patients undergoing abdominal surgery to reduce the risk of thromboemolic complications, patients undergoing knee or hip replacement therapy during and following the replacement procedure, as well as a general prophylactic to prevent clot formation at a later stage. The compounds, compositions and methods are further useful in the treatment of subjects that are under risk of thromboembolic complications due to severely restricted mobility e.g., during acute illness. Any such disorders may be readily treated by the compositions described herein. The therapeutic methods include both medical therapeutic and/or prophylactic administration, as appropriate.

As used herein, the term "inhibits platelet aggregation" includes its generally accepted meaning which includes prohibiting, slowing, or reducing the severity or degree of platelet aggregation. Such an inhibition may be measured as a function of time taken for a given sample to coagulate. In other embodiments, animal models of thrombosis. Methods of determining the efficacy of the agents include coagulation testing, monitoring the time of bleeding, determining hemoglobin levels of an animal and the like.

VI. Combination Therapy

The invention further provides combination therapy, wherein the compounds and/or compositions of the invention are administered with one or more additional agent(s) In general, the therapeutic methods, compositions and compounds may also be employed in combination with other therapeutics in the treatment of various disease states, with the additional agents being administered concurrently or sequentially with a composition of the invention.

A. Cytokines

Exemplary cytokines or hematopoietic factors for such co-administration include IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), angiopoietins, for example Ang-1, Ang-2, Ang-4, Ang-Y, the human angiopoietin-like polypeptides ANGPTL1 through 7, vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-S, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2a, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β3 binding protein III, thymic stromal lymphopoietin (TSLP), tumor necrosis factor receptor type I, tumor necrosis factor receptor type II, urokinase-type plasminogen activator receptor, vascular endothelial growth factor, and chimeric proteins and biologically or immunologically active fragments thereof.

B. Atherosclerosis Drugs

Additional active agents may act in complementary or synergistic ways with the modified LCAT protein when used to treat, and prevent atherosclerosis or manage cholesterol, or related disorders such as cardiovascular disease.

In one aspect, compounds of the invention can be used with statins. Statins are drugs that competitively inhibit 3-hydroxy-3-methylglutaryl coenzyme A reductase "HMG-CoA reductase," which is the enzyme that catalyzes an early, rate-limiting step in cholesterol biosynthesis. Hebert et al., JAMA 1997, 278: 313-21. This combination, in addition to raising HDL levels and lowering LDL levels may also lowers triglyceride and reduce inflammation. It is believed that the combination can have additional therapeutic effects, for example, the combination may lower blood pressure; protect against heart disease, for example, by reducing smooth muscle proliferation, reduce heart attacks, reduce platelet aggregation, and to reduce strokes as well as peripheral arterial disease (clogging of the arteries to the legs).

Examples of statins of the invention include, but are not limited to, mevastatin, pitavastatin, rosuvastatin, pentostatin (Nipent®), nystatin, lovastatin (Mevacor®), simvastatin (Zocor®), pravastatin (Pravachol®), fluvastatin (Lescol®), atorvastatin (Lipitor®), cerivastatin (Baycol®), or combinations thereof. Statins suitable for use in the compositions and methods of the invention are also disclosed in U.S. Pat. Nos. 4,681,893; 5,273,995; 5,356,896; 5,354,772; 5,686,104; 5,969,156; and 6,126,971. As some statins may exist in an inactive form, such as a lactone (e.g., simvastatin), the invention encompasses using the active form (e.g., b-hydroxy acid form) of them. See Physicians Desk Reference, 54.sup.th Ed. (2000) pp. 1917-1920.

Fibrates or fibric acid derivatives are regarded as broad-spectrum lipid-modulating agents in that although their main action is to decrease serum triglycerides they also tend to reduce LDL-cholesterol and to raise HDL-cholesterol. It is believed that the combined use of compounds of the invention and a fibrate may reduce the risk of coronary heart disease events in those with low HDL-cholesterol or with raised triglycerides by speeding up the chemical breakdown (i.e., catabolism) of triglyceride-rich lipoproteins that circulate in the body.

Fibrates include, but are not limited to, bezafibrate, ciprofibrate, fenofibrate, gemfibrozil, clofibrate, or combinations thereof. Fibrates suitable for inclusion in the compositions or administration in the methods of the invention are disclosed in U.S. Pat. Nos. 4,895,762; 6,074,670; and 6,277,405.

Biguanides for use in the compositions and methods of the invention include, but are not limited to, metformin, phenformin, buformin, or combinations thereof. Biguanides suitable for use in the compositions or methods of the invention are also disclosed in U.S. Pat. No. 6,303,146. The combined use of compounds of the invention and a bigaunide may improve glycemic control by enhancing insulin sensitivity in the liver and in muscle. The combination may reduce or avoid cardiovascular risk factors such as dyslipidemia, elevated plasminogen activator inhibitor 1 levels, other fibrinolytic abnormalities, hyperinsulinemia, insulin resistance, and is an effective and safe therapeutic agent for the treatment of type 2 diabetes.

In another aspect, compounds of the invention may be used in combination with glitazones, which may increase glucose uptake in muscle and reduced endogenous glucose production. Glitazones include 5-((4-(2-(methyl-2-pyridinyl amino) ethoxy)-phenyl)methyl)-2,4-thiazolidinedione, troglitazone, pioglitazone, ciglitazone, WAY-120,744, englitazone, AD 5075, darglitazone, rosiglitazone, combinations thereof, or a pharmaceutically acceptable salt, solvate, clathrate, polymorph, prodrug, or pharmacologically active metabolite thereof. Glitazones suitable for use in the compositions or methods of the invention are disclosed in U.S. Pat. Nos. 4,687,777; 5,002,953; 5,741,803; 5,965,584; 6,150,383; 6,150,384; 6,166,042; 6,166,043; 6,172,090; 6,211,205; 6,271,243; 6,288,095; 6,303,640; and 6,329,404.

Compositions comprising modified LCAT proteins of the invention and a sulfonylurea or a derivative thereof may increase insulin release from the pancreas and may further insulin levels by reducing hepatic clearance of the hormone. Sulfonylurea-based drugs for use the compositions and methods of the invention include, but are not limited to, glisoxepid, glyburide, acetohexamide, chlorpropamide, glibomuride, tolbutamide, tolazamide, glipizide, gliclazide, gliquidone, glyhexamide, phenbutamide, tolcyclamide, combinations thereof, or a pharmaceutically acceptable salt, solvate, or clathrate.

Combination compositions may also include agents that inhibit CETP. Such agents are, for example, Torcetrapib, and S-(2-[([1-(2-ethylbutyl)cyclohexyl]carbonyl)amino]phenyl)-2-methylpropanethioate.

Additional active agents also include cardiovascular drugs. Cardiovascular drugs for use in combination with the compounds of the invention to prevent or treat cardiovascular diseases include peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., aminone, milrinone, enoximone, fenoximone, imazodan, sulmazole), antidysrhythmic drugs, calcium entry blockers, ranitine, bosentan, and rezulin.

Depending on the disorder for which treatment is sought, compounds and compositions of the invention are used in combination therapy with other therapeutics that achieve a specific biological effect.

1. Cholesterol Lowering Drugs

Various medications can lower blood cholesterol levels. They may be prescribed individually or in combination with other drugs. Some of the common types of cholesterol-lowering drugs include statins, resins and nicotinic acid (niacin), gemfibrozil and clofibrate. Thus, combination therapy is contemplated utilizing, for example, clofibrate (Atromid-S, which raises the HDL cholesterol levels and lowers triglyceride levels), gemfibrozil (Lopid, which raises HDL cholesterol levels), nicotinic acid (which works in the liver by affecting the production of blood fats and is used to lower triglycerides and LDL cholesterol, and raise HDL ("good") cholesterol), resins (which are also called bile acid-binding drugs and work in the intestines by promoting increased disposal of cholesterol), including cholestyramine (Questran, Prevalite, Lo-Cholest), colestipol (Colestid) and colesevelam (WelChol), and statins including atorvastatin (Lipitor), fluvastatin (Lescol), lovastatin (Mevacor), pravastatin (Pravachol), rosuvastatin calcium (Crestor), and simvastatin (Zocor).

The drugs of first choice for elevated LDL cholesterol are the HMG CoA reductase inhibitors, e.g., atorvastatin, fluvastatin, lovastatin, pravastatin, rosuvastatin and simvastatin.

Statin drugs are effective for lowering LDL cholesterol levels, have few immediate short-term side effects, are easy to administer, have high patient acceptance and have few drug-drug interactions.

Another class of drugs for lowering LDL is the bile acid sequestrants—colesevelam, cholestyramine and colestipol—and nicotinic acid (niacin), which have been shown to reduce the risk for coronary heart disease in controlled clinical trials. Both classes of drugs appear to be free of serious side effects. But both can have troublesome side effects and require considerable patient education to achieve adherence. Nicotinic acid can be used by patients with triglyceride levels that exceed 250 mg/dL because bile acid sequestrants tend to raise triglyceride levels.

2. ACE Inhibitors

Angiotensin II causes blood vessels to contract and thereby narrows the blood vessels. The narrowing of the vessels increases the pressure within the vessels and can cause high blood pressure (hypertension). Angiotensin II is formed from angiotensin I in the blood by the enzyme, angiotensin converting enzyme (ACE). ACE inhibitors decrease the production of angiotensin II. As a result, the blood vessels enlarge or dilate, and the blood pressure is reduced. ACE inhibitors that available in the United States include captopril (Capoten), benazepril (Lotensin), enalapril (Vasotec), lisinopril (Prinivil, Zestril) fosinopril (Monopril), ramipril (Altace), perindopril (Aceon), quinapril (Accupril), moexipril (Univasc), and trandolapril (Mavik).

C. Anti-Inflammatory Drugs

In prevention and treatment of inflammation, combination therapy is contemplated with, for example, acetylsalicylic acid (Aspirin, Ecotrin), choline magnesium salicylate (Trilisate), diclofenac (Voltaren, Cataflam, Voltaren-XR), diflunisal (Dolobid), etodolac (Lodine), fenoprofen (Nalfon), flurbiprofen (Ansaid), ibuprofen (Advil, Motrin, Medipren, Nuprin), indomethacin (Indocin, Indocin-SR), ketoprofen (Orudis, Oruvail), meclofenamate (Meclomen), nabumetone (Relafen), naproxen (Naprosyn, Naprelan, Anaprox, Aleve), oxaprozin (Daypro), phenylbutazone (Butazolidine), piroxicam (Feldene), salsalate (Disalcid, Salflex), tolmetin (Tolectin), valdecoxib (Bextra), and COX-2 selective non-steroidal anti-inflammatory drugs (NSAIDs) including Bextra, Celebrex, Naproxen, and Vioxx. Prescription-only NSAIDs include ibuprofen (Brufen), aceclofenac (Preservex), acemetacin (Emflex), azapropazone (Rheumox), celecoxib (Celebrex), dexketoprofen (Keral), diclofenac (Voltarol, Diclomax, Arthrotec), diflusinal (Dolobid), etodolac (Lodine), fenbufen (Lederfen), fenoprofen (Fenopron), flurbiprofen (Froben), indometacin, ketoprofen (Orudis, Oruvail), mefenamic acid, meloxicam (Mobic), nabumetone (Relifex), naproxen (Naprosyn, Synflex), phenylbutazone (Butacote), piroxicam (Feldene), sulindac (Clinoril), tenoxicam (Mobiflex) and tiaprofenic acid (Surgam), D. Anti-Thrombosis Drugs In methods for prevention and treatment of thrombosis-related conditions, combination therapy is contemplated with anti-thrombosis drugs such as anticoagulant drugs, which inhibit the ability of blood to clot, or coagulate and include dalteparin (Fragmin), danaparoid (Orgaran), enoxaparin (Lovenox), heparin (various), tinzaparin (Innohep), warfarin (Coumadin), and lepirudin (Refludan), and antiplatelet drugs such as aspirin, ticlopidine (Ticlid), clopidogrel (Plavix), tirofiban (Aggrastat) and eptifibatide (Integrilin). Still other methods include the use of bivalirudin (selective and reversible thrombin inhibitor), argatroban (reversible inhibitor of thrombin), and low molecular weight heparins (LMWHs), including enoxaparin (Lovenox), dalteparin (Fragmin), ardeparin (Normiflo) fondaparinux and idraparinux. Still other anti-thrombosis drugs contemplated for use in methods of the invention include fragmin (dalteparin sodium injection) lovenox (enoxaparin sodium), Normiflo (ardeparin sodium), Orgaran (danaparoid sodium), indirect (Antithrombin-Dependent) FXa inhibitors such as fondaparinux (Arixtra®) and idraparinux, direct (Antithrombin-Independent) FXa inhibitors such as BAY 59-7939 [Bayer], DPC-423 [Bristol-Myers Squibb], DX-9065a [Daiichi], LY517717, razaxaban (DPC906), lepirudin (Refludan®), desirudin (Revasc®), bivalirudin (Hirulog®, Angiomax®), argatroban (Novastan®), melagatran, and ximelagatran (Exanta®).

It should be understood that the disorder that may be treated by the compositions of the present invention are limited only by the fact that the disorder needs a therapeutic intervention which inhibits platelet aggregation. The doses of the agent may be modified for each individual subject. For particular guidance on the routes of administration, and uses those of skill in the art are referred to the Physician's Desk Reference for generalized descriptions of formulations, routes of administration and patient monitoring used for agents such as Aggrastat™ (see e.g., entry at pages 1933-1937, PDR, 57th Edn., 2003), Aggrenox™ (see e.g., entry at pages 1023-1026, PDR, 57th Edn., 2003), Agrylin™ (see e.g., entry at pages 3142-3143, PDR, 57th Edn., 2003), Flolan™ (see e.g., entry at pages 1516-1521, PDR, 57th Edn., 2003), Integrilin™ (see e.g., entry at pages 2138-2142, PDR, 57th Edn., 2003), Presantine™ (see e.g., entry at pages 1052-2053, PDR, 57th Edn., 2003), Plavix™ (see e.g., entry at pages 1098-1101, PDR, 57th Edn., 2003), Pletal™ (see e.g., entry at pages 2780-2782, PDR, 57th Edn., 2003), REoPro™ (see e.g., entry at pages 1866-1870, PDR, 57th Edn., 2003), Coumdin™ (see e.g., entry at pages 1074-1079, PDR, 57th Edn., 2003), Fragmin™ (see e.g., entry at pages 2750-2754, PDR, 57th Edn., 2003), Hep-Lock™ (see e.g., entry at pages 1284-1288, PDR, 57th Edn., 2003), Lovenox™ (see e.g., entry at pages 739-744, PDR, 57th Edn., 2003), Miradon™ (see e.g., entry at pages 3051-3052, PDR, 57th Edn., 2003). These entries in the PDR are provided to show the level of skill in the art relating to formulating and using compositions as anticoagulants and anti-platelet agents.

E. Anti-Diabetic Drug.

Combination therapy using anti-diabetic drugs that lower blood glucose levels is also contemplated. Except for insulin, exenatide, and pramlintide, antidiabetics are administered orally and are thus also called oral hypoglycemic agents or oral antihyperglycemic agents. Antidiabetic drugs divided into six groups: insulin, sulfonylureas, alpha-glucosidase inhibitors, biguanides, meglitinides, and thiazolidinediones.

Insulin (Humulin, Novolin) controls blood glucose levels. Forms include isophane insulin suspension, insulin zinc suspension, and other formulations that extend the duration of insulin action. Use of inhaled forms of insulin are also contemplated.

Sulfonylureas increase insulin release from the beta cells of the pancreas, and include chlorpropamide [Diabinese], tolazamide [Tolinase], glipizide [Glucotrol], glimepiride (Amaryl), tolbutamide (Orinase), acetohexamide (Dymelor), glyburide (Diabeta, Micronase, Glynase), and gliclazide (Diamicron).

Alpha-glucosidase inhibitors inhibit the conversion of disaccharides and complex carbohydrates to glucose, and are used in combination therapy with sulfonylureas or other hypoglycemic agents. This type of anti-diabetic agent includes acarbose [Precose] and miglitol [Glyset].

The biguanide class of compounds mentioned above decreases hepatic glucose production, decreases intestinal absorption of glucose and increases peripheral glucose uptake and use.

The meglitinide class of compounds stimulates insulin production and may be used in combination with metformin. This class includes repaglinide (Prandin) and nateglitinide (Starlix).

Thiazolidinedione agent reduce glucose production in the liver and increase insulin-dependent glucose uptake in muscle cells. These agents may be used in combination with metformin or a sulfonylurea, and include rosiglitazone (Avandia) and pioglitazone (Actos).

Combination therapy with anti-diabetic peptide analogs is also contemplated. Such analogs include incretins which are insulin secretagogues, including glucagon-like peptide-1 (GLP-1) and gastric inhibitory peptide (also known as glucose-dependent insulinotropic peptide or GIP). Both GLP-1 and GIP are inactivated by the dipeptidyl peptidase-4 (DPP-4). Other peptides include Exenatide (also Exendin-4, sold as Byetta) which is a GLP agonist. and is more resistant to degradation by DPP-4; dipeptidyl peptidase-4 (DPP-4) inhibitors which maintain blood concentration of GLP-1 by inhibiting its degradation by dipeptidyl peptidase-4 (DPP-4), this class of peptides including vildagliptin and sitagliptin, and amylin agonist analogues which slow gastric emptying and suppress glucagons, this type including pramlintide It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below.

Example 1

Preparation of Modified LCAT Protein

A polynucleotide encoding wild type human LCAT protein (SEQ ID NO: 1) was cloned from human liver cDNA library. DNA encoding the wild type human LCAT protein was mutagenized using Quickchange site-directed mutagenesis kit (Stratagene) well known and routinely utilized in the art.

Briefly, primer pairs containing the designed mutations were incorporated into the newly synthesized DNA molecules. The newly synthesized LCAT coding sequence was tagged with a polynucleotide encoding human Fc fragment at the C-terminus of the encoded protein. The parental template was digested with Dpn I endonuclease. The nicked vector DNA containing the desired mutants was transformed into XL1-Blue E. coli. Plasmids encoding mutant LCAT were recovered from the transformed E. coli. The presence of the mutations in the plasmids was confirmed by DNA sequencing analysis and the mutant LCAT-Fc constructs were transfected into CHO cells for protein expression using DHFR-based vector set and chemically-defined media. Recombinant human LCAT-Fc (rhLCAT-Fc) fusion mutant proteins (i.e., modified LCAT proteins) were isolated from culture media of transfected CHO cells. Productions (i.e., fermentations) have involved growth of transfected CHO cells in either shaker flasks or bioreactor vessels with rhLCAT-Fc secreted to the medium.

Purification of Fc-fused modified human LCAT proteins was performed as follows. Cultures were typically harvested after 4-6 days of protein production and crude supernatant was isolated from cells via centrifugation or hollow fiber filtration for shaker flask and bioreactor productions, respectively. The crude mixture was then either loaded directly or concentrated 10×-20× and buffer-exchanged into 20 mM sodium phosphate, pH 7.2, 300 mM NaCl, 0.05% azide and loaded onto mAbSelect Sure resin (GE Biosciences). The resin was then washed with the same high salt phosphate buffer 5-10 times and the bound protein was eluted with 300 mM citrate, pH 3.4. Eluted fractions were neutralized with 1 M Tris buffer, pH 8.0. In order to enrich the Protein A affinity purified material to greater than 90% full-length protein, high-resolution Hydrophobic Interaction Chromatography (HIC) chromatography was utilized. A pH-neutralized pool was loaded directly onto a pre-packed Biosuite Phenyl HIC column (Waters) resulting in the bulk of the clipped species flowing through, and the bulk of the full-length protein adhering to the column. Modified LCAT-Fc proteins were eluted via a linear gradient to 100% Milli-Q $H_2O$. Fractions were analyzed for percentage of the full-length LCAT via N-terminal sequence (NTS) and were pooled accordingly. An HIC pool was then concentrated and further purified via preparative size-exclusion chromatography (SEC) with PBS, pH 7.2, 10% glycerol, 50 µM EDTA as the mobile phase. The non-aggregated SEC product was concentrated to 5 mg/mL if necessary, aliquoted and flash frozen.

Example 2

Screens for Modified LCAT Proteins

LCAT Enzyme Activity

Activity of the modified LCAT proteins was determined by measuring the change of the rate of conversion of $^3$H-labeled cholesterol (FC) to cholesteryl ester (CE). In the plasma LCAT activity assay (CER), human plasma samples were equilibrated with a trace amount of radiolabeled cholesterol at 4° C. and the rate of cholesterol esterification was measured by thin layer chromatography (TLC) analysis after incubation at 37° C. (Dobiasova and Frohlich, Physiol Res. 1996; 45, 65-73).

For measuring compound activity using apoAI-liposome assay format, modified LCAT protein was expressed in CHO cells and enzyme secreted from the stably transfected cells was harvested in the serum-free culture medium. The activity of the modified LCAT enzyme in the culture media was determined using apoAI-liposome substrates prepared by the standard cholate-dialysis procedure (Chen et al. (1982) J. Lipid Res. 23: 680-691). The initial mixture contained egg phosphatidylcholine (PC) (Sigma), /$^3$H-unesterfied cholesterol/human apoAI (molar ratio of 250:12.5:0.8). After dialysis the proteoliposomes were incorporated with the modified LCAT protein. LCAT activity was determined by measuring the conversion of radiolabeled cholesterol to cholesteryl ester and expressed in nmol CE/mL per hour. The activity of the modified LCAT enzyme in the purified form was measured using the same assay, except that recombinant LCAT protein was purified either with standard Protein A-affinity colume that specifically recognized the Fc fusion fragment of the recombinant protein, or with affinity resin that specifically recognize the His tag of the recombinant protein. LCAT activity of purified samples was expressed in nmol CE/µg/hour.

Activity ranges of the exemplary modified LCAT proteins are summarized in Table 3.

TABLE 3

| Position | Modified LCAT protein | LCAT Activity (nmol/h/μg) |
|---|---|---|
| Wild type | Wild type sequence | + |
| | Addition of Q before first amino acid | ++ |
| | Addition of P between amino acids 1 and 2 | ++ |
| | Using mouse Kappa chain signal peptide | ++ |
| | Using human IgG1 signal peptide | ++ |
| | N-terminal human IgG1 Fc-fusion | − |
| | Addition of FWLLNV at N-terminal | ++ |
| | Addition of FWLLNVLFPP at N-terminal | ++ |
| | Addition of FWLLNVLFPP at C-terminal | +++ |
| F1 | F1A | ++ |
| | F1G | ++ |
| | F1I | ++ |
| | F1L | ++ |
| | F1M | ++ |
| | F1P | ++ |
| | F1V | ++ |
| | F1C | ++ |
| | F1W | +++ |
| | F1Y | ++ |
| | F1T | ++ |
| | F1S | +++ |
| | F1Q | ++ |
| | F1N | ++ |
| | F1H | ++ |
| | F1D | ++ |
| L3 | L3I | ++ |
| | L3F | ++ |
| | L3C | ++ |
| | L3W | ++ |
| | L3Y | ++ |
| | L4A | ++ |
| L4 | L4I | ++ |
| | L4M | ++ |
| | L4F | ++ |
| | L4V | ++ |
| | L4W | ++ |
| | L4Y | ++ |
| | L4T | ++ |
| | L4Q | ++ |
| | L4R | ++ |
| | N5A | ++ |
| N5 | N5M | ++ |
| | N5M | ++ |
| | N5H | ++ |
| | N5K | ++ |
| | N5D | ++ |
| | N5E | ++ |
| V6 | L7M | ++ |
| | L7F | ++ |
| | L7E | ++ |
| | C31A | ++ |
| | C31I | +++ |
| L7 | C31M | ++ |
| | C31F | +++ |
| | C31V | ++ |
| | C31C | ++ |
| | C31W | ++ |
| | C31Y | +++ |
| | C31T | ++ |
| | C31R | ++ |
| | C31H | ++ |
| | N384C | ++ |
| C31 | N384Q | ++ |
| | E416C | ++ |
| | F1A-C31Y | ++ |
| | L4F-C31Y | +++ |
| | N4E-C31Y | ++ |
| | N5Q-C31Y | ++ |
| | N5D-C31Y | +++ |
| | N5A-C31Y | +++ |
| T246N | V28A-C31I | ++ |
| N384 | V28I-C31I | ++ |
| W2-C31 | V28C-C31I | ++ |
| N5-C31 | V28T-C31I | ++ |
| L4-C31 | V28R-C31I | ++ |
| N5-C31 | P29GC31-I | ++ |
| | P29F-C31I | ++ |
| | P29T-C31I | ++ |
| V28-C31 | G30A-C31I | ++ |
| | G30I-IC31 | ++ |
| | C21I-L32A | ++ |
| | IC31-IL32 | ++ |
| | C31I-L32M | ++ |
| | C31I-L32F | +++ |
| | C31I-L32C | ++ |
| | C31I-L32W | ++ |
| | C31I-L32Y | ++ |
| | C31I-L32T | ++ |
| | C31I-L32S | ++ |
| | C31I-L32N | ++ |
| | C31I-L32H | +++ |
| P29-C31 | C31I-L32E | ++ |
| | C31I-G33I | ++ |
| | C31I-G33M | ++ |
| | C31I-G33F | ++ |
| | C31I-G33S | ++ |
| | C31I-G33H | ++ |
| | C31I-N34A | ++ |
| G30-C31 | G30A-C31I | ++ |
| | G30I-IC31 | ++ |
| C31-L32 | C21I-L32A | ++ |
| | IC31-IL32 | ++ |
| | C31I-L32M | ++ |
| | C31I-L32F | +++ |
| | C31I-L32C | ++ |
| | C31I-L32W | ++ |
| | C31I-L32Y | ++ |
| | C31I-L32T | ++ |
| | C31I-L32S | ++ |
| | C31I-L32N | ++ |
| | C31I-L32H | +++ |
| | C31I-L32E | ++ |
| C31-G33 | C31I-G33I | ++ |
| | C31I-G33M | ++ |
| | C31I-G33F | ++ |
| | C31I-G33S | ++ |
| | C31I-G33H | ++ |
| C31-N34 | C31I-N34A | ++ |
| | C31I-N34C | ++ |
| | C31I-N34S | ++ |
| | C31I-N34R | +++ |

As used herein,
"+" is the activity of the wild type protein;
"++" - LCAT enzymatic activity is in the range from −20% to +50% of wild type protein activity;
"+++" - LCAT activity is at least 50% higher than that of the wild type protein as measured in the same experimental setting.
"−" indicates that activity is below detectable level.

Modified LCAT proteins with enzymatic activity of at least 20% higher than that of the wild type LCAT protein were purified on a larger scale for determining the N-terminal sequences of the modified LCAT protein. Modified LCAT proteins maintaining intact N-terminal sequence without any clipping, were subjected to further evaluation of stability and in vivo efficacy.

In Vivo Efficacy and Stability of the Modified LCAT Protein Entities

Modified LCAT protein molecules were evaluated in animal models including mice, hamsters and rabbits. The readouts for in vivo evaluation included efficacy of increasing plasma HDL-Cholesterol (HDL-C) levels and stability (PK). Animals of choice were treated with single dosing or multiple dosing of modified LCAT protein and during the period of time up to 255 hours, plasma samples were isolated from animals and measurements were conducted.

HDL-C was determined enzymatically using Polyethylene Glycol (PGE)—modified enzyme and dextran sulfate, as described in the manual of HDL-C plus $3^{rd}$ generation kit, cobas, (Cat. No. 04713311 190), and using automated analyzer Roche/Hitachi 904/911/912/MODULAR analyzers CAN 435.

PK was measured as follows. Briefly, the assay used for determining-recombinant LCAT-Fc protein concentrations was a sandwich ELISA method developed at Amgen. Mouse anti-LCAT clone 9B14A12 was diluted in phosphate buffered saline (PBS), then coated onto the wells of a 96-well microtiter plate (Maxisorp, Nunc) and incubated overnight at 5°±3° C. The plate was washed 3 times with 1× KPL Wash Buffer. A blocking buffer comprised of 10% non-fat dried milk (NFDM) in PBS+0.05% Tween-20 (PBST) was dispensed into the wells. After a minimum of one-hour ambient room temperature (ART) incubation without agitation, the blocking buffer was removed from the wells. Next, the LCAT-Fc assay standards, NSB, and quality control samples (QCs), which were prepared in 100% New Zealand white rabbit serum and pretreated at a dilution factor of 50 in PBST+10% NFDM, were added to the plate along with rabbit serum specimens that were also pretreated in PBST+10% NFDM. Following a one-hour ART incubation with agitation, the plate was washed six times with 1×KPL Wash Buffer, then a horseradish peroxidase-labeled goat anti-rabbit Fc with minimal cross-reactivity to human serum protein (Jackson; #111-035-046) was diluted at a dilution factor of 25,000 in 10% NFDM containing 2% pooled rabbit serum and added to the wells for detection of LCAT-Fc. After a one-hour ART incubation with agitation, the plate was washed and developed using TMB substrate solution (1:1 tetramethylbenzidine and peroxide, Kirkegaard & Perry Laboratories). The resulting colorimetric reaction was quenched with 1+9 phosphoric acid (VWR; #VW3346-1) after a ten-minute ART incubation and optical densities (ODs) were determined at a wavelength of 450-650 nm. The conversion of OD values into concentrations for the QCs and unknown specimens was achieved through Watson software mediated comparison to a concurrently analyzed standard curve, which was regressed according to a four-parameter logistic model with a weighting factor of 1.

Results showed that tested modified LCAT protein had improved stability compared to wild type LCAT protein and that HDL was robustly increased in a dose dependent manner. Modified LCAT protein molecules showing efficacy in raising plasma HDL-C levels and acceptable in vivo stability were further analyzed in preclinical atherosclerosis models.

Atherosclerosis Animal Models

This study involved the use of wild type New Zealand White (NZW) rabbits. Animals were treated with atherogenic (high-cholesterol) diet for 4 months to induce atherosclerosis, followed with the treatment using modified LCAT for atherosclerosis regression. Animals were divided into 4 groups for treatments: a) vehicle; b) low rLCAT dose and c) high rLCAT dose; and d) no treatment but terminating the animals for basal line of plaque lesion, respectively. The treatment duration was set for 8-16 weeks depending on if adverse effects occur along the course. At the end of the treatment atherosclerotic lesions were evaluated. The procedure for assessing atherosclerotic plaque was as following.

Briefly, animals were anesthetized using pentobarbital and then saline perfusion was conducted, followed by fixation with paraformaldehyde. Aorta was isolated by removing all attached organs and fat tissues and split from distal to proximal. Aorta was then pinned on wax plates and stained using Sudan IV. Light microscope photograph was used to quantify plaque lesion area and stain was analyzed using Image-Pro software.

Example 3

Recombinant LCAT Protein with Double Mutations

In view of the activity measurements observed above with various LCAT mutations, a number of double mutants comprising a C31Y substitution and an additional substitution, as shown below, were prepared and assessed for activity by the ability to convert of radiolabeled cholesterol (FC) into cholesteryl ester (CE), as described before.

Results are shown below in Table 4 with the double mutants compared to wild-type protein and the single mutant C31Y LCAT protein. As used in Table 4, "−" indicates enzyme activity was below the detection level; "+" is shown as the wild-type LCAT protein activity; "++" indicates enzyme activity was in the range of −20% to +50% of wild-type protein activity; "+++" indicates activity in the range of +100% to +500% of wild-type protein activity; and "++++" indicates enzyme activity greater than +500% of wild-type LCAT activity.

TABLE 4

| LCAT Protein | LCAT activity (nmol/h/µg) |
| --- | --- |
| Wild-type | + |
| C31Y | +++ |
| C31Y, F1S | +++ |
| C31Y, F1W | ++++ |
| C31Y, L4M | ++ |
| C31Y, L4K | + |
| C31Y, N34S | +++ |
| C31Y, L32F | +++ |
| C31Y, L32H | +++ |
| C31Y, L7N | − |

Example 4

In Vivo Comparison Between Wild-Type and Modified LCAT Proteins

In order to individually assess in vivo activity of a modified LCAT protein compared to wild-type LCAT individually, the following experiment was carried out.

Recombinant wild-type LCAT protein and modified LCAT comprising a C31Y substitution were expressed in stably transfected CHO cells. The C31Y modified LCAT was expressed and an Fc fusion protein, the Fc vehicle derived from either human- or Rabbit-IgG. The wild-type human protein was expressed with a carboxy terminal histidine (His) tag and purified with affinity beads that that specifically bind this tag. The C31Y modified LCAT-Fc protein was purified using Protein A affinity beads. Both forms of purified rLCAT proteins were solubilized in buffer containing PBS pH 7.2, 50 µM EDTA and 10% glycerol.

Wild-type mice were fed normal chow prior to the study. Animals (n=4 per group) were administered a single dose of either wild-type or modified proteins at 10 mg/kg via IV injection and blood samples were collected at certain time points over the following two weeks. Serum from each sample was assessed for wild-type or modified LCAT protein content using standard ELISA. Protein activity was assessed by conversion of radiolabeled cholesterol (FC) into cholesteryl ester (CE). Plasma lipids—total cholesterol (TC), high density lipoprotein C (HDL-C) and triglycerides (TG)-were measured using a clinical analyzer.

Results indicated that the wild-type LCAT protein was isolated from CHO cells culture emdia having a molecular weight of 70 kD and an activity of 20 nmol CE/hr/µg. Wild-type protein was shown to have a half-life of less than 30 minutes, and plasma LCAT activity within 2 hours after administration increased by 30 to 40%. No change was detected in plasma HDL-C levels over the course of the study.

In contrast, the recombinant human C31Y modified LCAT protein was isolated from the host cells culture media with a molecular weight of 95 kD (monimer) and showed an activity of 200 nmol CE/hr/µg. Half-life for the protein after administration was determined to be approximately 3 days, and within 3 days after administration plasma LCAT activity increased up to 400%. In addition, plasma HDL-C levels showed approximately 3.5 fold increase 24 hours after administration and lasted for about three days before returned to the basal level.

Example 5

Modified LCAT Activity Assessment

Experiments were designed to assess the ability of a modified LCAT protein to restore ApoA-I and HDL-C levels in LCAT-knockout mice (LCAT knockout mice were generated as described in publication The Journal of Biological Chemistry, 1997; 272: 15777-15781).

In brief, a group of wild type and LCAT-knockout mice (n=4 per group) were fed with normal chow before the study. Animals were then treated by IV injection of either modified recombinant human LCAT protein [rhLCAT(C31Y)-huFc] at 10 mg/kg, or vehicle buffer of equal volume (PBS pH 7.2, 50 µM EDTA, 10% glycerol). Approximately 24 hours after injection, animals were terminated and blood samples collected. Serum samples were isolated from blood. Plasma LCAT activity was determined by the conversion of radiolabeled cholesterol (FC) into cholesteryl ester (CE) with use of apoAI-proteoliposome as the substrate. Plasma apoA-1 protein levels were determined by Western blotting with use of anti-mouse apoAI antibody. Plasma lipids (TC, HDL-C and TG) were measured by clinical analyzer.

Results showed that treatment with the modified rhLCAT protein increased plasma LCAT activity in wild type mice and restored plasma LCAT activity in LCAT-knockout mice. In addition, treatment with the modified rhLCAT protein restored plasma apoAI protein levels in LCAT-knockout mice to approximately normal levels (i.e., wild-type mouse levels), as measured with Western Blotting. Further, treatment with the modified rhLCAT protein restored plasma HDL-C levels in LCAT-knockout mice to approximately wild-type mouse level, as measured with clinical analyzer indicated. Finally, treatment with the modified rhLCAT protein suppressed the elevated TG levels in LCAT-knockout mice to the same as wild-type mouse levels with the same treatment, also as measured.

Example 6

Additional In Vivo Assessment of Modified LCAT Activity

In another series of experiments, modified rhLCAT activity was assessed in vivo to determine its effect on HDL-C levels in rabbits.

In brief, New Zealand White rabbits (body weight 2 kg each) were fed with normal chow before the study. Animals were then randomized into three groups with each group (n=4) receiving treatment of either vehicle buffer (PBS pH 7.2, 50 µM EDTA, 10% glycerol), or recombinant rabbit LCAT(C31Y)-rab Fc protein dosed at 1.0 mg/kg, or 10.0 mg/kg, respectively. At the indicated time points, blood samples were collected for analyses. Serum samples were isolated from blood. Plasma LCAT activity was determined by the conversion of radiolabeled cholesterol (FC) into cholesteryl ester (CE) with use of apoAI-proteoliposome as the substrate. Plasma lipids (TC, HDL-C and TG) were measured by clinical analyzer. Pooled serum samples from same group of animals were used in FPLC fractionation, and cholesterol and TG contents in each fraction were determined by clinical analyzer.

Results showed that treatment with the modified rLCAT protein rapidly increased plasma LCAT activity in time- and dose-dependent manners and also robustly increased plasma HDL-C levels, also in time- and dose-dependent manners. In addition, the modified rLCAT protein modulated HDL particles dose-dependently and reversibly without increasing plasma LDL or VLDL levels, as indicated with FPLC analysis.

Example 7

Immunogenicity Studies

Immunogenicity studies were carried out in order to determine whether a modified LCAT protein sequence would elicit an unfavorable immune response in humans.

In brief, two LCAT protein peptides were assessed via in silico methods for their potential to induce an immune response. One peptide was 33 residues in length with the wild-type LCAT amino acid sequence. The other peptide was also 33 amino acids in length, but included a C16Y modification of the wild-type LCAT sequence, the C16Y mutation corresponding to the C31Y LCAT sequence mutation.

Results showed that the wild-type peptide induced a low immune response. Surprisingly, even though the mutant C16Y peptide was predicted to induce a higher immune response, it was found that the actual immune response was quite low. In view of this result, it is believed that the modified C31Y LCAT protein is unlikely to induce an anti-therapeutic response when administered in vivo.

The combination of data in this in other examples herein indicates that while a wild-type LCAT protein is less likely to induce an immune response, the higher activity of the modified LCAT protein, and the low capacity for the modified protein to induce an immune response, makes the modified LCAT protein a highly desirable therapeutic alternative to the wild-type protein.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A modified lecithin-cholesterol acyltransferase (LCAT) protein comprising a modified form of the mature human LCAT amino acid sequence set out in SEQ ID NO:1 or SEQ ID NO:2, wherein the modification to the LCAT protein sequence consists of a substitution at amino acid residue C31, and wherein the modified LCAT protein has increased LCAT enzymatic activity compared to the LCAT protein of SEQ ID NO:1 or 2 as measured in a cholesterol esterification rate (CER) plasma LCAT activity assay.

2. The modified LCAT protein of claim 1 wherein the substitution at position C31 is C31I, C31M, C31F, C31V, C31W, C31Y, C31T, C31R, or C31H.

3. The modified LCAT protein of claim 2 wherein the substitution at position C31 is C31Y.

4. The modified LCAT protein of claim 1 further comprising a vehicle.

5. The modified LCAT protein of claim 4 wherein the vehicle is selected from the group consisting of an immunoglobulin constant (Fc) region, a water soluble polymer, and polyethylene glycol.

6. The modified LCAT protein of claim 4 wherein the vehicle is an immunoglobulin constant (Fc) region.

7. A pharmaceutical composition comprising a modified LCAT protein of claim 1 and a pharmaceutically acceptable carrier.

8. A method of treating a lecithin-cholesterol acyltransferase (LCAT) related disorder comprising the step of administering an amount of a modified LCAT protein of claim 1 in an amount effective to treat said disorder.

9. The method of claim 8, wherein the modified LCAT (i) is administered intravenously as an infusion, or (ii) is administered intravenously as a bolus.

10. The method of claim 8, wherein the LCAT-related disorder is selected from the group consisting of atherosclerosis, inflammation, thrombosis, coronary heart disease, high blood pressure, LCAT deficiency syndrome, corneal opacity, dyslipidemia, myocardial infarction, stroke, critical limb ischemia, and angina.

11. A method for increasing HDL cholesterol in a subject comprising administering to the subject a therapeutically effective amount of a modified LCAT protein of claim 1.

12. A method for decreasing accumulation of cholesterol in a subject comprising administering a therapeutically effective amount of a modified LCAT protein of claim 1.

13. A modified lecithin-cholesterol acyltransferase (LCAT) protein comprising a modified form of the mature human LCAT amino acid sequence set out in SEQ ID NO:1 or SEQ ID NO:2, wherein the modifications to the LCAT protein sequence consist of a substitution at amino acid residue C31 and a substitution at an amino acid residue position selected from the group consisting of F1, L3, L4, N5, L7, N384 and E416, and wherein the modified LCAT protein has increased LCAT enzymatic activity compared to the LCAT protein of SEQ ID NO: 1 or 2 as measured in a cholesterol esterification rate (CER) plasma LCAT activity assay.

14. The modified LCAT protein of claim 13 wherein the substitution at amino acid residue C31 is C31A, C31I, C31M, C31F, C31V, C31W, C31Y, C31T, C31R, or C31H and the substitution at amino acid residue F1, L3, L4, N5, L7, N384 or E416 is F1A, F1G, F1I, F1L, F1M, F1P, F1V, F1C, F1Y, F1T, F1Q, F1N, F1H, F1D, L3I, L3F, L3C, L3W, L3Y, L4A, L4I, L4M, L4F, L4V, L4W, L4Y, L4T, L4Q, L4R, N5A, N5M, N5H, N5K, N5D, N5E, L7M, L7F, L7E, N384C, N384Q or E416C.

15. The modified LCAT protein of claim 13 further comprising a vehicle.

16. The modified LCAT protein of claim 15 wherein the vehicle is selected from the group consisting of an immunoglobulin constant (Fc) region, a water soluble polymer, and polyethylene glycol.

17. The modified LCAT protein of claim 15 wherein the vehicle is an immunoglobulin constant (Fc) region.

18. A pharmaceutical composition comprising a modified LCAT protein of claim 13 and a pharmaceutically acceptable carrier.

19. A method of treating a lecithin-cholesterol acyltransferase (LCAT) related disorder comprising the step of administering an amount of a modified LCAT protein of claim 13 in an amount effective to treat said disorder.

20. The method of claim 19, wherein the modified LCAT (i) is administered intravenously as an infusion, or (ii) is administered intravenously as a bolus.

21. The method of claim 19, wherein the LCAT-related disorder is selected from the group consisting of atherosclerosis, inflammation, thrombosis, coronary heart disease, high blood pressure LCAT deficiency syndrome, corneal opacity, myocardial infarction, stroke, critical limb ischemia, and angina.

22. A method for increasing HDL cholesterol in a subject comprising administering to the subject a therapeutically effective amount of a modified LCAT protein of claim 13.

23. A method for decreasing accumulation of cholesterol in a subject comprising administering a therapeutically effective amount of a modified LCAT protein of claim 13.

24. A modified lecithin-cholesterol acyltransferase (LCAT) protein comprising a modified form of the mature human LCAT amino acid sequence set out in SEQ ID NO:1 or SEQ ID NO:2 wherein the modifications to the LCAT protein sequence consist of a substitution at amino acid residue C31 and a substitution at an amino acid residue position selected from the group consisting of F1, L4, N5, V28, P29, G30, L32, G33 and N34, and wherein the modified LCAT protein has increased LCAT enzymatic activity compared to the LCAT protein of SEQ ID NO: 1 or 2 as measured in a cholesterol esterification rate (CER) plasma LCAT activity assay.

25. The modified LCAT protein of claim 24 wherein the substitution at the amino acid residue position F1, L4, N5, V28, P29, G30, L32, G33 or N34 is selected from the group consisting of F1A, L4F, N5E, N5Q, N5D, N5A, V28A, V28I, V28C, V28T, V28R, P29G, P29F, P29T, G30A, G30I, L32A, L32I, L32M, L32F, L32C, L32W, L32Y, L32T, L32S, L32N, L32H, L32E, G33I, G33M, G33F, G33S, G33H, N34A, N34C, N34S and N34R.

26. The modified LCAT protein of claim 25 wherein the C31 amino acid substitution is C31I, C31F, or C31Y.

27. The modified LCAT protein of claim 26 wherein the C31 amino acid substitution is C31Y.

28. The modified LCAT protein of claim 27 wherein the substitution at F1, L4, L32 or N34 is F1S, F1W, L4M, L4K, N34S, L32F, and L32H.

29. The modified LCAT protein of claim 28, wherein the modified LCAT protein consists of a C31Y substitution and an L4M or L4K substitution.

30. The modified LCAT protein of claim 28, wherein the modified LCAT protein consists of a C31Y substitution and an L32F substitution.

31. The modified LCAT protein of claim 24 further comprising a vehicle.

32. The modified LCAT protein of claim 31 wherein the vehicle is selected from the group consisting of an immunoglobulin constant (Fc) region, a water soluble polymer, and polyethylene glycol.

33. The modified LCAT protein of claim 31 wherein the vehicle is an immunoglobulin constant (Fc) region.

34. A pharmaceutical composition comprising a modified LCAT protein of claim 24 and a pharmaceutically acceptable carrier.

35. A method of treating a lecithin-cholesterol acyltransferase (LCAT) related disorder comprising the step of administering an amount of a modified LCAT protein of claim 24 in an amount effective to treat said disorder.

36. The method of claim 35, wherein the modified LCAT (i) is administered intravenously as an infusion, or (ii) is administered intravenously as a bolus.

37. The method of claim 35, wherein the LCAT-related disorder is selected from the group consisting of atherosclerosis, inflammation, thrombosis, coronary heart disease, high blood pressure, LCAT deficiency syndrome, corneal opacity, dyslipidemia, myocardial infarction, stroke, critical limb ischemia, and angina.

38. A method for increasing HDL cholesterol in a subject comprising administering to the subject a therapeutically effective amount of a modified LCAT protein of claim 24.

39. A method for decreasing accumulation of cholesterol in a subject comprising administering a therapeutically effective amount of a modified LCAT protein of claim 24.

40. A modified lecithin-cholesterol acyltransferase (LCAT) protein comprising a modified form of the mature human LCAT amino acid sequence set out in SEQ ID NO:1 or SEQ ID NO:2, wherein the modifications to the LCAT protein sequence consist of a C31Y substitution and an N5D substitution, and wherein the modified LCAT protein has increased LCAT enzymatic activity compared to the LCAT protein of SEQ ID NO:1 or SEQ ID NO:2 as measured in a cholesterol esterification rate (CER) plasma LCAT activity assay.

41. The modified LCAT protein of claim 40 further comprising a vehicle.

42. The modified LCAT protein of claim 41 wherein the vehicle is selected from the group consisting of an immunoglobulin constant (Fc) region, a water soluble polymer, and polyethylene glycol.

43. The modified LCAT protein of claim 41 wherein the vehicle is an immunoglobulin constant (Fc) region.

44. A pharmaceutical composition comprising a modified LCAT protein of claim 40 and a pharmaceutically acceptable carrier.

45. A method of treating a lecithin-cholesterol acyltransferase (LCAT) related disorder comprising the step of administering an amount of a modified LCAT protein of claim 40 in an amount effective to treat said disorder.

46. The method of claim 45, wherein the modified LCAT (i) is administered intravenously as an infusion, or (ii) is administered intravenously as a bolus.

47. The method of claim 45, wherein the LCAT-related disorder is selected from the group consisting of atherosclerosis, inflammation, thrombosis, coronary heart disease, high blood pressure LCAT deficiency syndrome, corneal opacity, dyslipidemia, myocardial infarction, stroke, critical limb ischemia, and angina.

48. A method for increasing HDL cholesterol in a subject comprising administering to the subject a therapeutically effective amount of a modified LCAT protein of claim 40.

49. A method for decreasing accumulation of cholesterol in a subject comprising administering a therapeutically effective amount of a modified LCAT protein of claim 40.

50. A modified lecithin-cholesterol acyltransferase (LCAT) protein comprising a modified form of the mature human LCAT amino acid sequence set out in SEQ ID NO:1 or SEQ ID NO:2, wherein the modifications to the LCAT protein sequence consist of a C31Y substitution and an L4W substitution, and wherein the modified LCAT protein has increased LCAT enzymatic activity compared to the LCAT protein of SEQ ID NO:1 or SEQ ID NO:2 as measured in a cholesterol esterification rate (CER) plasma LCAT activity assay.

51. The modified LCAT protein of claim 50 further comprising a vehicle.

52. The modified LCAT protein of claim 51 wherein the vehicle is selected from the group consisting of an immunoglobulin constant (Fc) region, a water soluble polymer, and polyethylene glycol.

53. The modified LCAT protein of claim 51 wherein the vehicle is an immunoglobulin constant (Fc) region.

54. A pharmaceutical composition comprising a modified LCAT protein of claim 50 and a pharmaceutically acceptable carrier.

55. A method of treating a lecithin-cholesterol acyltransferase (LCAT) related disorder comprising the step of administering an amount of a modified LCAT protein of claim 50 in an amount effective to treat said disorder.

56. The method of claim 55, wherein the modified LCAT (i) is administered intravenously as an infusion, or (ii) is administered intravenously as a bolus.

57. The method of claim 55, wherein the LCAT-related disorder is selected from the group consisting of atherosclerosis, inflammation, thrombosis, coronary heart disease, high blood pressure, LCAT deficiency syndrome, corneal opacity, dyslipidemia, myocardial infarction, stroke, critical limb ischemia, and angina.

58. A method for increasing HDL cholesterol in a subject comprising administering to the subject a therapeutically effective amount of a modified LCAT protein of claim 50.

59. A method for decreasing accumulation of cholesterol in a subject comprising administering a therapeutically effective amount of a modified LCAT protein of claim 50.

60. A modified lecithin-cholesterol acyltransferase (LCAT) protein comprising a modified form of the mature human LCAT amino acid sequence set out in SEQ ID NO:1 or SEQ ID NO:2, wherein the modifications to the LCAT protein sequence consist of a C31Y substitution, an L4F substitution and an N5D substitution, and wherein the modified LCAT protein has increased LCAT enzymatic activity compared to the LCAT protein of SEQ ID NO:1 or SEQ ID NO:2 as measured in a cholesterol esterification rate (CER) plasma LCAT activity assay.

61. The modified LCAT protein of claim 60 further comprising a vehicle.

62. The modified LCAT protein of claim 61 wherein the vehicle is selected from the group consisting of an immunoglobulin constant (Fc) region, a water soluble polymer, and polyethylene glycol.

63. The modified LCAT protein of claim 61 wherein the vehicle is an immunoglobulin constant (Fc) region.

64. A pharmaceutical composition comprising a modified LCAT protein of claim 60 and a pharmaceutically acceptable carrier.

65. A method of treating a lecithin-cholesterol acyltransferase (LCAT) related disorder comprising the step of administering an amount of a modified LCAT protein of claim 60 in an amount effective to treat said disorder.

66. The method of claim 65, wherein the modified LCAT (i) is administered intravenously as an infusion, or (ii) is administered intravenously as a bolus.

67. The method of claim 65, wherein the LCAT-related disorder is selected from the group consisting of atherosclerosis, inflammation, thrombosis, coronary heart disease, high blood pressure, LCAT deficiency syndrome, corneal opacity, dyslipidemia, myocardial infarction, stroke, critical limb ischemia, and angina.

68. A method for increasing HDL cholesterol in a subject comprising administering to the subject a therapeutically effective amount of a modified LCAT protein of claim 60.

69. A method for decreasing accumulation of cholesterol in a subject comprising administering a therapeutically effective amount of a modified LCAT protein of claim 60.

* * * * *

UNITED STATES PATENT AND TRADEMARK OFFICE
CERTIFICATE OF CORRECTION

| | | |
|---|---|---|
| PATENT NO. | : 8,168,416 B2 | Page 1 of 1 |
| APPLICATION NO. | : 12/179815 | |
| DATED | : May 1, 2012 | |
| INVENTOR(S) | : Boone et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 58 days.

Signed and Sealed this

Eleventh Day of September, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,168,416 B2 |
| APPLICATION NO. | : 12/179815 |
| DATED | : May 1, 2012 |
| INVENTOR(S) | : Tom Boone et al. |

It is certified that error appears in the above-identified patent and that said Letters Patent is hereby corrected as shown below:

In the Claims:

At Column 50, Claim 21, lines 65-66, "opacity, myocardial" should be -- opacity, dyslipidemia, myocardial --.

Signed and Sealed this
Second Day of October, 2012

David J. Kappos
*Director of the United States Patent and Trademark Office*

SEQUENCE LISTING

<160> NUMBER OF SEQ ID NOS: 2

<210> SEQ ID NO 1
<211> LENGTH: 416
<212> TYPE: PRT
<213> ORGANISM: Homo sapiens

<400> SEQUENCE: 1

```
Phe Trp Leu Leu Asn Val Leu Phe Pro Pro His Thr Thr Pro Lys Ala
1               5                   10                  15

Glu Leu Ser Asn His Thr Arg Pro Val Ile Leu Val Pro Gly Cys Leu
            20                  25                  30

Gly Asn Gln Leu Glu Ala Lys Leu Asp Lys Pro Asp Val Val Asn Trp
        35                  40                  45

Met Cys Tyr Arg Lys Thr Glu Asp Phe Phe Thr Ile Trp Leu Asp Leu
    50                  55                  60

Asn Met Phe Leu Cys Leu Gly Val Asp Cys Trp Ile Asp Asn Thr Arg
65                  70                  75                  80

Val Val Tyr Asn Arg Ser Ser Gly Leu Val Ser Asn Ala Pro Gly Val
                85                  90                  95

Gln Ile Arg Val Pro Gly Phe Gly Lys Thr Tyr Ser Val Glu Tyr Leu
            100                 105                 110

Asp Ser Ser Lys Leu Ala Gly Tyr Leu His Thr Leu Val Gln Asn Leu
        115                 120                 125

Val Asn Asn Gly Tyr Val Arg Asp Glu Thr Val Arg Ala Ala Pro Tyr
130                 135                 140

Asp Trp Arg Leu Glu Pro Gly Gln Gln Glu Glu Tyr Tyr Arg Lys Leu
145                 150                 155                 160

Ala Gly Leu Val Glu Glu Met His Ala Ala Tyr Gly Lys Pro Val Phe
                165                 170                 175

Leu Ile Gly His Ser Leu Gly Cys Leu His Leu Leu Tyr Phe Leu Leu
            180                 185                 190

Arg Gln Pro Gln Ala Trp Lys Asp Arg Phe Ile Asp Gly Phe Ile Ser
        195                 200                 205

Leu Gly Ala Pro Trp Gly Gly Ser Ile Lys Pro Met Leu Val Leu Ala
210                 215                 220

Ser Gly Asp Asn Gln Gly Ile Pro Ile Met Ser Ser Ile Lys Leu Lys
225                 230                 235                 240

Glu Glu Gln Arg Ile Thr Thr Thr Ser Pro Trp Met Phe Pro Ser Arg
                245                 250                 255

Met Ala Trp Pro Glu Asp His Val Phe Ile Ser Thr Pro Ser Phe Asn
            260                 265                 270

Tyr Thr Gly Arg Asp Phe Gln Arg Phe Phe Ala Asp Leu His Phe Glu
        275                 280                 285

Glu Gly Trp Tyr Met Trp Leu Gln Ser Arg Asp Leu Leu Ala Gly Leu
290                 295                 300

Pro Ala Pro Gly Val Glu Val Tyr Cys Leu Tyr Gly Val Gly Leu Pro
305                 310                 315                 320

Thr Pro Arg Thr Tyr Ile Tyr Asp His Gly Phe Pro Tyr Thr Asp Pro
                325                 330                 335

Val Gly Val Leu Tyr Glu Asp Gly Asp Asp Thr Val Ala Thr Arg Ser
            340                 345                 350

Thr Glu Leu Cys Gly Leu Trp Gln Gly Arg Gln Pro Gln Pro Val His
        355                 360                 365
```

```
Leu Leu Pro Leu His Gly Ile Gln His Leu Asn Met Val Phe Ser Asn
    370             375                 380
Leu Thr Leu Glu His Ile Asn Ala Ile Leu Leu Gly Ala Tyr Arg Gln
385             390                 395                 400
Gly Pro Pro Ala Ser Pro Thr Ala Ser Pro Glu Pro Pro Pro Glu
                405                 410                 415

<210> SEQ ID NO 2
<211> LENGTH: 424
<212> TYPE: PRT
<213> ORGANISM: Homo sapiens
<220> FEATURE:
<221> NAME/KEY: mat_peptide
<222> LOCATION: (9)..(424)

<400> SEQUENCE: 2

Leu Leu Leu Pro Pro Ala Ala Pro Phe Trp Leu Leu Asn Val Leu Phe
            -5              -1  1               5
Pro Pro His Thr Thr Pro Lys Ala Glu Leu Ser Asn His Thr Arg Pro
        10              15                  20
Val Ile Leu Val Pro Gly Cys Leu Gly Asn Gln Leu Glu Ala Lys Leu
25              30                  35                  40
Asp Lys Pro Asp Val Val Asn Trp Met Cys Tyr Arg Lys Thr Glu Asp
                45                  50                  55
Phe Phe Thr Ile Trp Leu Asp Leu Asn Met Phe Leu Pro Leu Gly Val
                60                  65                  70
Asp Cys Trp Ile Asp Asn Thr Arg Val Val Tyr Asn Arg Ser Ser Gly
            75                  80                  85
Leu Val Ser Asn Ala Pro Gly Val Gln Ile Arg Val Pro Gly Phe Gly
    90                  95                  100
Lys Thr Tyr Ser Val Glu Tyr Leu Asp Ser Ser Lys Leu Ala Gly Tyr
105                 110                 115                 120
Leu His Thr Leu Val Gln Asn Leu Val Asn Asn Gly Tyr Val Arg Asp
                125                 130                 135
Glu Thr Val Arg Ala Ala Pro Tyr Asp Trp Arg Leu Glu Pro Gly Gln
            140                 145                 150
Gln Glu Glu Tyr Tyr Arg Lys Leu Ala Gly Leu Val Glu Glu Met His
        155                 160                 165
Ala Ala Tyr Gly Lys Pro Val Phe Leu Ile Gly His Ser Leu Gly Cys
    170                 175                 180
Leu His Leu Leu Tyr Phe Leu Leu Arg Gln Pro Gln Ala Trp Lys Asp
185                 190                 195                 200
Arg Phe Ile Asp Gly Phe Ile Ser Leu Gly Ala Pro Trp Gly Gly Ser
                205                 210                 215
Ile Lys Pro Met Leu Val Leu Ala Ser Gly Asp Asn Gln Gly Ile Pro
                220                 225                 230
His Met Ser Ser Ile Lys Leu Lys Glu Glu Gln Arg Ile Thr Thr Thr
            235                 240                 245
Ser Pro Trp Met Phe Pro Ser Arg Met Ala Trp Pro Glu Asp His Val
    250                 255                 260
Phe Ile Ser Thr Pro Ser Phe Asn Tyr Thr Gly Arg Asp Phe Gln Arg
265                 270                 275                 280
Phe Phe Ala Asp Leu His Phe Glu Glu Gly Trp Tyr Met Trp Leu Gln
                285                 290                 295
Ser Arg Asp Leu Leu Ala Gly Leu Pro Ala Pro Gly Val Glu Val Tyr
            300                 305                 310
```

```
Cys Leu Tyr Gly Val Gly Leu Pro Thr Pro Arg Thr Tyr Ile Tyr Asp
        315                 320                 325

His Gly Phe Pro Tyr Thr Asp Pro Val Gly Val Leu Tyr Glu Asp Gly
        330                 335                 340

Asp Asp Thr Val Ala Thr Arg Ser Thr Glu Leu Cys Gly Leu Trp Gln
345                 350                 355                 360

Gly Arg Gln Pro Gln Pro Val His Leu Leu Pro Leu His Gly Ile Gln
                365                 370                 375

His Leu Asn Met Val Phe Ser Asn Leu Thr Leu Glu His Ile Asn Ala
                380                 385                 390

Ile Leu Leu Gly Ala Tyr Arg Gln Gly Pro Pro Ala Ser Pro Thr Ala
        395                 400                 405

Ser Pro Glu Pro Pro Pro Glu
        410                 415
```